(12) United States Patent
Zhang et al.

(10) Patent No.: US 7,972,850 B2
(45) Date of Patent: Jul. 5, 2011

(54) METHOD OF IN VITRO DIFFERENTIATION OF NEURAL STEM CELLS, MOTOR NEURONS AND DOPAMINE NEURONS FROM PRIMATE EMBRYONIC STEM CELLS

(75) Inventors: Su-Chun Zhang, Middleton, WI (US); Xue-jun Li, Madison, WI (US)

(73) Assignee: Wisonsin Alumni Research Foundation, Madison, WI (US)

( * ) Notice: Subject to any disclaimer, the term of this patent is extended or adjusted under 35 U.S.C. 154(b) by 689 days.

(21) Appl. No.: 11/594,455

(22) Filed: Nov. 8, 2006

(65) Prior Publication Data

US 2008/0206865 A1 Aug. 28, 2008

Related U.S. Application Data

(62) Division of application No. 10/928,805, filed on Aug. 27, 2004, now Pat. No. 7,588,937.

(60) Provisional application No. 60/498,831, filed on Aug. 29, 2003, provisional application No. 60/499,570, filed on Sep. 2, 2003.

(51) Int. Cl.
*C12N 5/00* (2006.01)
*C12N 5/02* (2006.01)
*C12N 5/08* (2006.01)
*A01N 63/00* (2006.01)
*A01N 65/00* (2006.01)

(52) U.S. Cl. ........................................ 435/377; 435/368

(58) Field of Classification Search ........................ None
See application file for complete search history.

(56) References Cited

U.S. PATENT DOCUMENTS

| | | | |
|---|---|---|---|
| 5,843,780 | A | 12/1998 | Thomson et al. |
| 6,200,806 | B1 | 3/2001 | Thomson et al. |
| 6,251,669 | B1 | 6/2001 | Luskin |
| 6,468,794 | B1 | 10/2002 | Uchida et al. |
| 6,497,872 | B1 | 12/2002 | Weiss et al. |
| 6,498,018 | B1 | 12/2002 | Carpenter |
| 6,833,269 | B2 | 12/2004 | Carpenter |
| 7,390,659 | B2 * | 6/2008 | Jessell et al. .................. 435/377 |
| 7,588,937 | B2 | 9/2009 | Zhang et al. |
| 2002/0009743 | A1 | 1/2002 | Carpenter |
| 2002/0028510 | A1 | 3/2002 | Sanberg et al. |
| 2002/0114788 | A1 | 8/2002 | Isacson et al. |
| 2002/0168763 | A1 | 11/2002 | Yan et al. |
| 2003/0068819 | A1 | 4/2003 | Zhang et al. |
| 2003/0211605 | A1 | 11/2003 | Lee et al. |
| 2003/0224411 | A1 | 12/2003 | Stanton et al. |
| 2004/0009592 | A1 | 1/2004 | Sabate et al. |
| 2008/0227137 | A1 | 9/2008 | Zhang et al. |

FOREIGN PATENT DOCUMENTS

| | | |
|---|---|---|
| CA | 2315538 A1 | 7/1999 |
| CA | 2443151 A1 | 10/2002 |
| GB | 2421029 | 4/2008 |
| SG | 119929 | 5/2007 |
| WO | 9416718 A1 | 8/1994 |
| WO | 9747734 A1 | 12/1997 |
| WO | 9920740 A2 | 4/1999 |
| WO | 9920741 A1 | 4/1999 |
| WO | 0151616 A2 | 7/2001 |
| WO | 0181549 A2 | 11/2001 |
| WO | 0183715 A2 | 11/2001 |
| WO | 0188104 A2 | 11/2001 |
| WO | 03104444 A1 | 12/2003 |
| WO | 2004015077 A2 | 2/2004 |
| WO | 2004042018 A2 | 5/2004 |
| WO | 2004081172 A2 | 9/2004 |
| WO | 2005/021720 A2 | 3/2005 |

OTHER PUBLICATIONS

Wichterle et al. Directed differentiation of embryonic stem cells into motor neurons. Cell 110:385-397, 2002.*
Li et al. Specification of motoneurons from human embryonic stem cells. Nature Biotechnology 23:215-221, 2005.*
Sockanathan et al. Motor Neuron-derived retinoid signaling specifies the subtype identity of spinal motor neurons. Cell 94:503-514, 1998.*
Liu et al. Assigning the positional identity of spinal motor neurons: Rostrocaudal patterning of Hox-c expression by FGFs, Gdf11, and retinoids. Neuron 32:997-1012, 2001.*
Sockanathan et al. Retinoid receptor signaling in postmitotic motor neurons regulates rostrocaudal positional identity and axonal projection pattern. Neuron 40:97-111, 2003.*
G. Bain, et al., "Embryonic Stem Cells Express Neuronal Properties in Vitro," Develop. Biol. 168: 342-357, 1995.
T. Mujtaba, et al., "Lineage-Restricted Neural Precursors Can Be Isolated from Broth the Mouse Neural Tube and Cultured ES Cells," Develop. Biol. 214: 113-127, 1999.
S.-H. Lee, et al., "Efficient Generation of Midbrain and Hindbrain Neurons from Mouse Embryonic Stem Cells," Nat. Biotechnol. 18:675-679, 2000.
S.-C. Zhang et al., "In Vitro Differentiation of Transplantable Nueral Precursors from Human Embryonic Stem Cells," Nat. Biotechnol. 19: 1129-1133, 2001.
Y. P. Yan et al., "Induction of Midbrain Dopamine Neurons from Human Embryonic Stem Cells," The Society for Neuroscience 33rd Annual Meeting, New Orleans, LA, Nov. 08, 2003.
X. J. Li et al., "Differentiation of Human Embryonic Stem Cells into Motoneurons," The Society for Neuroscience 33rd Annual Meeting, New Orleans, LA, Nov. 08, 2003.
A. L. Perrier et al., "Derivation of Midbrain Dopamine Neurons from Human Embryonic Stem Cells," Proc. Natl. Acad. Sci. USA 101: 12543-12548, 2004.
L. H. Penvy et al., "A Role of Sox1 in Neural Determination," Development 125: 1967-1978, 1998.
Y. Yan, et al., "Directed Differentiation of Dopaminergic Neuronal Subtypes from Human Embryonic Stem Cells," Stem Cells 23: 781-790, 2005.
X. Li, et al., "Specification of Motoneurons from Human Embryonic Stem Cells," Nat. Biotechnol. 23(2): 215-221, 2005.

(Continued)

*Primary Examiner* — Quang Nguyen
(74) *Attorney, Agent, or Firm* — Quarles & Brady, LLP

(57) ABSTRACT

A method of differentiating embryonic stem cells into neural and motor cells is disclosed. In one embodiment, the invention comprises culturing a population of cells comprising a majority of cells that are characterized by an early rosette morphology and are $Sox1^-/Pax6^+$ in the presence of FGF2, FGF4, FGF8, FGF 9, or RA wherein the cells are characterized by an neural tube-like rosette morphology and are $Pax6^+/Sox1^+$.

Figure 1:
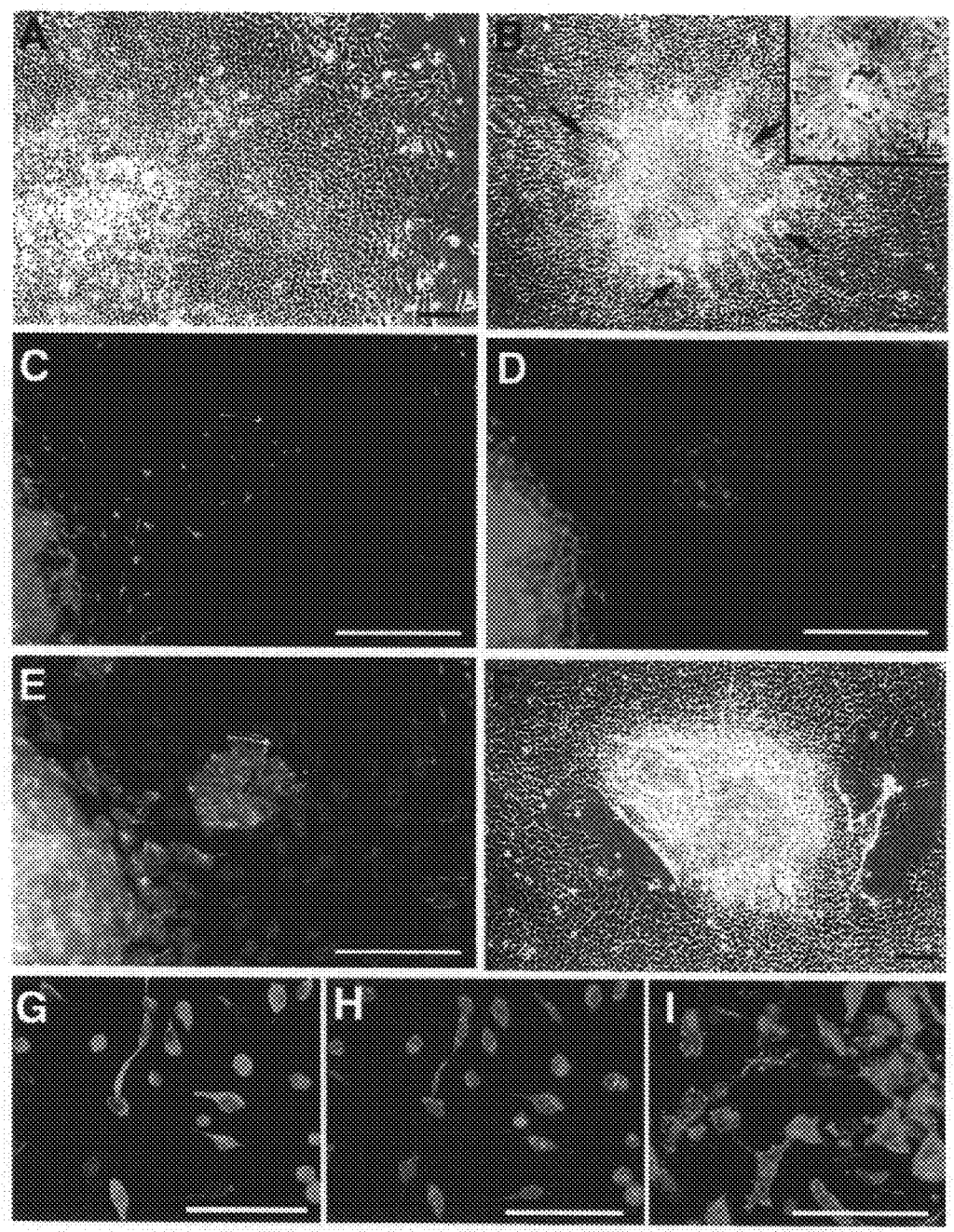

5 Claims, 13 Drawing Sheets
(13 of 13 Drawing Sheet(s) Filed in Color)

OTHER PUBLICATIONS

O. Brüstle, et al., "In Vitro-generated Neural Precursors Participate in Mammalian Brain Development," Proc. Natl. Acad. Sci. USA 94:14809-14814, 1997.

M. K. Carpenter, et al., "Enrichment of Neurons and Neural Precursors from Human Embryonic Stem Cells," Exp. Neurol. 172:383-397, 2001.

M. Kawata, et al., "Neural Rosette Formation within in Vitro Spheroids of a Clonal Human Tetracarcinoma Cell Line, PA-1/NR: Role of Extracellular Matrix Components in the Morphogenesis," Cancer Res. 51:2655-2669, 1991.

S.-C. Zhang, et al., Keystone Symposium on Pluripotent Stem Cells, Feb. 6, 2001 (Poster).

Ding S. & Schultz P., "A role for chemistry in stem cell biology," Nat. Biotechnol. 22:833-840 (2004).

Pankratz M, et al., "Directed neural differentiation of human embryonic stem cells via an obligated primitave anterior stage," Stem Cells, 25:1511-1520 (2007).

Wu X., et al., "Purmorphamine induces osteogenesis by activation of the hedgehog signaling pathway," Chem. Biol. 11:1299-1238 (2004).

* cited by examiner

SEQUENCE LISTING

```
<160> NUMBER OF SEQ ID NOS: 32

<210> SEQ ID NO 1
<211> LENGTH: 20
<212> TYPE: DNA
<213> ORGANISM: Artificial
<220> FEATURE:
<223> OTHER INFORMATION: Synthetic PCR primer

<400> SEQUENCE: 1
accacagtcc atgccatcac                                              20

<210> SEQ ID NO 2
<211> LENGTH: 20
<212> TYPE: DNA
<213> ORGANISM: Artificial
<220> FEATURE:
<223> OTHER INFORMATION: Synthetic PCR primer

<400> SEQUENCE: 2
tccaccaccc tgttgctgta                                              20

<210> SEQ ID NO 3
<211> LENGTH: 23
<212> TYPE: DNA
<213> ORGANISM: Artificial
<220> FEATURE:
<223> OTHER INFORMATION: Synthetic PCR primer

<400> SEQUENCE: 3
cgatgccttg tgttcaggcg cag                                          23

<210> SEQ ID NO 4
<211> LENGTH: 23
<212> TYPE: DNA
<213> ORGANISM: Artificial
<220> FEATURE:
<223> OTHER INFORMATION: Synthetic PCR primer

<400> SEQUENCE: 4
agcctttgca gccctcacag gtg                                          23

<210> SEQ ID NO 5
<211> LENGTH: 20
<212> TYPE: DNA
<213> ORGANISM: Artificial
<220> FEATURE:
<223> OTHER INFORMATION: Synthetic PCR primer

<400> SEQUENCE: 5
gtgggtggag aggagaacaa                                              20

<210> SEQ ID NO 6
<211> LENGTH: 21
<212> TYPE: DNA
<213> ORGANISM: Artificial
<220> FEATURE:
<223> OTHER INFORMATION: Synthetic PCR primer

<400> SEQUENCE: 6
```
ttcctccctc aggaaacaat g                                         21

<210> SEQ ID NO 7
<211> LENGTH: 21
<212> TYPE: DNA
<213> ORGANISM: Artificial
<220> FEATURE:
<223> OTHER INFORMATION: Synthetic PCR primer

<400> SEQUENCE: 7
gggatcggaa actgttactg c                                         21

<210> SEQ ID NO 8
<211> LENGTH: 20
<212> TYPE: DNA
<213> ORGANISM: Artificial
<220> FEATURE:
<223> OTHER INFORMATION: Synthetic PCR primer

<400> SEQUENCE: 8
gtagtcaccc ttgcacagca                                           20

<210> SEQ ID NO 9
<211> LENGTH: 20
<212> TYPE: DNA
<213> ORGANISM: Artificial
<220> FEATURE:
<223> OTHER INFORMATION: Synthetic PCR primer

<400> SEQUENCE: 9
ccctggtttc tctgggactt                                           20

<210> SEQ ID NO 10
<211> LENGTH: 20
<212> TYPE: DNA
<213> ORGANISM: Artificial
<220> FEATURE:
<223> OTHER INFORMATION: Synthetic PCR primer

<400> SEQUENCE: 10
gcagtctgtg gggtcgtatt                                           20

<210> SEQ ID NO 11
<211> LENGTH: 21
<212> TYPE: DNA
<213> ORGANISM: Artificial
<220> FEATURE:
<223> OTHER INFORMATION: Synthetic PCR primer

<400> SEQUENCE: 11
tttatggggc tcagcaagag g                                         21

<210> SEQ ID NO 12
<211> LENGTH: 22
<212> TYPE: DNA
<213> ORGANISM: Artificial
<220> FEATURE:
<223> OTHER INFORMATION: Synthetic PCR primer

<400> SEQUENCE: 12
tccacttcat ccttcggttc tg                                        22

<210> SEQ ID NO 13
<211> LENGTH: 20
<212> TYPE: DNA
<213> ORGANISM: Artificial
<220> FEATURE:

<223> OTHER INFORMATION: Synthetic PCR primer

<400> SEQUENCE: 13
tcggggtgct tccttgtagc                                            20

<210> SEQ ID NO 14
<211> LENGTH: 20
<212> TYPE: DNA
<213> ORGANISM: Artificial
<220> FEATURE:
<223> OTHER INFORMATION: Synthetic PCR primer

<400> SEQUENCE: 14
ttcgtggcag ggactatggg                                            20

<210> SEQ ID NO 15
<211> LENGTH: 20
<212> TYPE: DNA
<213> ORGANISM: Artificial
<220> FEATURE:
<223> OTHER INFORMATION: Synthetic PCR primer

<400> SEQUENCE: 15
aactccacct tccccgtcac                                            20

<210> SEQ ID NO 16
<211> LENGTH: 20
<212> TYPE: DNA
<213> ORGANISM: Artificial
<220> FEATURE:
<223> OTHER INFORMATION: Synthetic PCR primer

<400> SEQUENCE: 16
cttctgtctc gccgaacacg                                            20

<210> SEQ ID NO 17
<211> LENGTH: 20
<212> TYPE: DNA
<213> ORGANISM: Artificial
<220> FEATURE:
<223> OTHER INFORMATION: Synthetic PCR primer

<400> SEQUENCE: 17
caacagcaga atggaggtca                                            20

<210> SEQ ID NO 18
<211> LENGTH: 20
<212> TYPE: DNA
<213> ORGANISM: Artificial
<220> FEATURE:
<223> OTHER INFORMATION: Synthetic PCR primer

<400> SEQUENCE: 18
ctgggtggaa agagaagctg                                            20

<210> SEQ ID NO 19
<211> LENGTH: 20
<212> TYPE: DNA
<213> ORGANISM: Artificial
<220> FEATURE:
<223> OTHER INFORMATION: Synthetic PCR primer

<400> SEQUENCE: 19
tcagaaggag acggaggcta                                            20

<210> SEQ ID NO 20

```
<211> LENGTH: 20
<212> TYPE: DNA
<213> ORGANISM: Artificial
<220> FEATURE:
<223> OTHER INFORMATION: Synthetic PCR primer

<400> SEQUENCE: 20
gtgggggtgt taggttctga                                              20

<210> SEQ ID NO 21
<211> LENGTH: 22
<212> TYPE: DNA
<213> ORGANISM: Artificial
<220> FEATURE:
<223> OTHER INFORMATION: Synthetic PCR primer

<400> SEQUENCE: 21
aaggaggcag tggcttcaag tc                                           22

<210> SEQ ID NO 22
<211> LENGTH: 20
<212> TYPE: DNA
<213> ORGANISM: Artificial
<220> FEATURE:
<223> OTHER INFORMATION: Synthetic PCR primer

<400> SEQUENCE: 22
cgctcaccag tcgcttcatc                                              20

<210> SEQ ID NO 23
<211> LENGTH: 22
<212> TYPE: DNA
<213> ORGANISM: Artificial
<220> FEATURE:
<223> OTHER INFORMATION: Synthetic PCR primer

<400> SEQUENCE: 23
tgcctctcct tctgaacctt gg                                           22

<210> SEQ ID NO 24
<211> LENGTH: 20
<212> TYPE: DNA
<213> ORGANISM: Artificial
<220> FEATURE:
<223> OTHER INFORMATION: Synthetic PCR primer

<400> SEQUENCE: 24
gcgaaatctg ccaccagttg                                              20

<210> SEQ ID NO 25
<211> LENGTH: 20
<212> TYPE: DNA
<213> ORGANISM: Artificial
<220> FEATURE:
<223> OTHER INFORMATION: Synthetic PCR primer

<400> SEQUENCE: 25
aagaacgcca ccagggagag                                              20

<210> SEQ ID NO 26
<211> LENGTH: 20
<212> TYPE: DNA
<213> ORGANISM: Artificial
<220> FEATURE:
<223> OTHER INFORMATION: Synthetic PCR primer

<400> SEQUENCE: 26
```

```
ttggagtccg aaatgggtcc                                               20
```

<210> SEQ ID NO 27
<211> LENGTH: 20
<212> TYPE: DNA
<213> ORGANISM: Artificial
<220> FEATURE:
<223> OTHER INFORMATION: Synthetic PCR primer

<400> SEQUENCE: 27

```
ggcaacctac gcaagatggc                                               20
```

<210> SEQ ID NO 28
<211> LENGTH: 20
<212> TYPE: DNA
<213> ORGANISM: Artificial
<220> FEATURE:
<223> OTHER INFORMATION: Synthetic PCR primer

<400> SEQUENCE: 28

```
tgagggctgt gtctgttcgg                                               20
```

<210> SEQ ID NO 29
<211> LENGTH: 20
<212> TYPE: DNA
<213> ORGANISM: Artificial
<220> FEATURE:
<223> OTHER INFORMATION: Synthetic PCR primer

<400> SEQUENCE: 29

```
ccaattacaa ccccgacatc                                               20
```

<210> SEQ ID NO 30
<211> LENGTH: 20
<212> TYPE: DNA
<213> ORGANISM: Artificial
<220> FEATURE:
<223> OTHER INFORMATION: Synthetic PCR primer

<400> SEQUENCE: 30

```
ccgagttctc tgctttcacc                                               20
```

<210> SEQ ID NO 31
<211> LENGTH: 21
<212> TYPE: DNA
<213> ORGANISM: Artificial
<220> FEATURE:
<223> OTHER INFORMATION: Synthetic PCR primer

<400> SEQUENCE: 31

```
acacgagacc cacttttcc g                                              21
```

<210> SEQ ID NO 32
<211> LENGTH: 23
<212> TYPE: DNA
<213> ORGANISM: Artificial
<220> FEATURE:
<223> OTHER INFORMATION: Synthetic PCR primer

<400> SEQUENCE: 32

```
tgctggactt gtgcttcttc aac                                           23
```

METHOD OF IN VITRO DIFFERENTIATION OF NEURAL STEM CELLS, MOTOR NEURONS AND DOPAMINE NEURONS FROM PRIMATE EMBRYONIC STEM CELLS

CROSS-REFERENCE TO RELATED APPLICATIONS

This application is a divisional of the prior non-provisional U.S. patent application Ser. No. 10/928,805, filed Aug. 27, 2004, now U.S. Pat. No. 7,588,937 (incorporated herein) which claims priority to U.S. patent application Ser. No. 09/970,382, filed Oct. 3, 2001 (incorporated herein) and also claims priority to U.S. Provisional Patent Application 60/498,831, filed Aug. 29, 2003 (incorporated herein) and U.S. Provisional Patent Application Ser. No. 60/499,570, filed Sep. 2, 2003 (incorporated herein).

STATEMENT REGARDING FEDERALLY SPONSORED RESEARCH OR DEVELOPMENT

This invention was made with no United States government support.

BACKGROUND OF THE INVENTION

Human embryonic stem (ES) cells are pluripotent cells derived from the inner cell mass of pre-implantation embryos (Thomson, J. A., et al., *Science* 282:1145-1147, 1998). Similar to mouse ES cells, they can be expanded to large numbers while maintaining their potential to differentiate into various somatic cell types of all three germ layers (Thomson, J. A., et al., supra, 1998; Reubinoff, B. E., et al., *Nat. Biotech.* 18:399, 2000; Thomson, J. A. and Odorico, J. S., *Trends Biotech* 18:53-57, 2000; Amit, M., et al., *Dev. Biol.* 227:271-278, 2000). The in vitro differentiation of ES cells provides new perspectives for studying the cellular and molecular mechanisms of early development and the generation of donor cells for transplantation therapies. Indeed, mouse ES cells have been found to differentiate in vitro to many clinically relevant cell types, including hematopoietic cells (Wiles, M. V. and Keller, G., *Development* 111:259-267, 1991), cardiomyocytes (Klug, M. G., et al., *J. Clin. Invest.* 98:216-224, 1996), insulin-secreting cells (Soria, B., et al., *Diabetes* 49:157-162, 2000), and neurons and glia (Bain, G., et al., *Dev. Biol.* 168:342-357, 1995; Okabe, S., et al., *Mech. Dev.* 59:89-102, 1996; Mujtaba, T., et al., *Dev. Biol.* 214:113-127, 1999; Brustle, O., et al., *Science* 285:754-756, 1999). Following transplantation into the rodent central nervous system (CNS), ES cell-derived neural precursors have been shown to integrate into the host tissue and, in some cases, yield functional improvement (McDonald, J. W., et al., *Nat. Med.* 5:1410-1412, 1999). A clinical application of human ES cells would require the generation of highly purified donor cells for specific tissues and organs.

Needed in the art is a simple, yet efficient, strategy for the isolation of transplantable neural and motor neuron precursors from differentiating human ES cell cultures.

SUMMARY OF THE INVENTION

In one embodiment, the present invention is a method of creating a population of cells comprising a synchronous population of cells cultured from embryonic stem cells which are characterized by an early rosette morphology and are $Sox1^-$, $Pax6^+$. In one embodiment, the method comprises the steps of: (a) propagating embryonic stem cells into embryoid bodies and (b) propagating embryoid bodies into a synchronous population of neural stem cells in the form of neural tube-like rosettes, wherein this propagation is in the presence of FGF2, FGF8, FGF4 or FGF9. The total time period between the propagation of embryonic stem cells to development of early rosettes is preferably 8-10 days. Preferably, the total population of $Pax6^+/Sox1^-$ cells is at least 70% of the total cell population.

The present invention is also a population of cells created by this method.

In another embodiment, the invention is a method of creating a population of synchronized neural stem cells wherein the cells are characterized by a neural tube-like rosette morphology and are $Pax6^+/Sox1^+$, the method comprising the step of culturing cells that are characterized by an early rosette morphology and are $Sox1^-$, $Pax6^+$ for 4-6 days in the presence of FGF2, FGF4, FGF8, or RA. The invention is also a population of cells created by this method.

In one embodiment, the early rosette cells were cultured with FGF8, preferably for 4-7 days, and are $EN1^+$. In another embodiment, the cells were cultured with FGF2, preferably for 4-7 days, and are $Bf1^+$. In another embodiment, the cells were cultured with RA, preferably for 4-7 days, and are $Hox^+$.

In another embodiment, the invention is a method of isolating a population of midbrain dopamine neurons, comprising the step of culturing the cells described above in the presence of FGF8 with SHH, wherein the resulting cells express TH, AADC, EN-1, VMAT2 and DAT, but do not express DbH and PNMT. The invention is also a population of cells created by this method.

In another embodiment, the invention is a method of isolating a population of spinal motor neurons comprising the step of culturing the cells above described above in the presence of RA with SHH, wherein the resulting cells express HB9, HoxB1, HoxB6, HoxC5, HoxC8, ChAT and VAChT. The invention is also a population of cells created by this method.

In another embodiment, the present invention is a method of isolating a population of forebrain dopamine neurons comprising the step of culturing the cells described above with SHH. The invention is also a population of cells created by this method.

The present invention is also a method of testing the cell populations described above to screen agents for the ability to affect normal human neural development.

Other objects, advantages and features of the present invention will become apparent after review of the specification, claims and drawings.

DETAILED DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

FIG. 1A-I. Differentiation and isolation of neural precursors from ES cells. (FIG. 1A) An attached EB grown in the presence of FGF2 for five days shows flattened cells at the periphery and small elongated cells congregated in the center. (FIG. 1B) By seven days, many rosette formations (arrows) appeared in the differentiating EB center. The upper-right inset is the 1-μm section of the rosette stained with toluidine blue, showing columnar cells arranged in a tubular structure. Bar=20 μm. (FIG. 1C-E) Cells in a cluster of rosettes (lower left) and a small forming rosette (center) are positive for nestin (FIG. 1C) and Musashi-1 (FIG. 1D) whereas the surrounding flat cells are negative. (FIG. 1E) A combined image of FIG. 1C and FIG. 1D with all cell nuclei labeled with DAPI. (FIG. 1E) After treatment with dispase for 20 minutes, the rosette formations retracted whereas the surrounding flat cells remained attached. (FIG. 1G-I) Isolated cells are positively stained for nestin in a filamentous pattern (FIG. 1G), Musashi-1 in cytoplasm (FIG. 1H), and PSA-NCAM mainly on membrane (FIG. 1I). All nuclei are stained with DAPI. Bar=100 μm.

Figure 2:
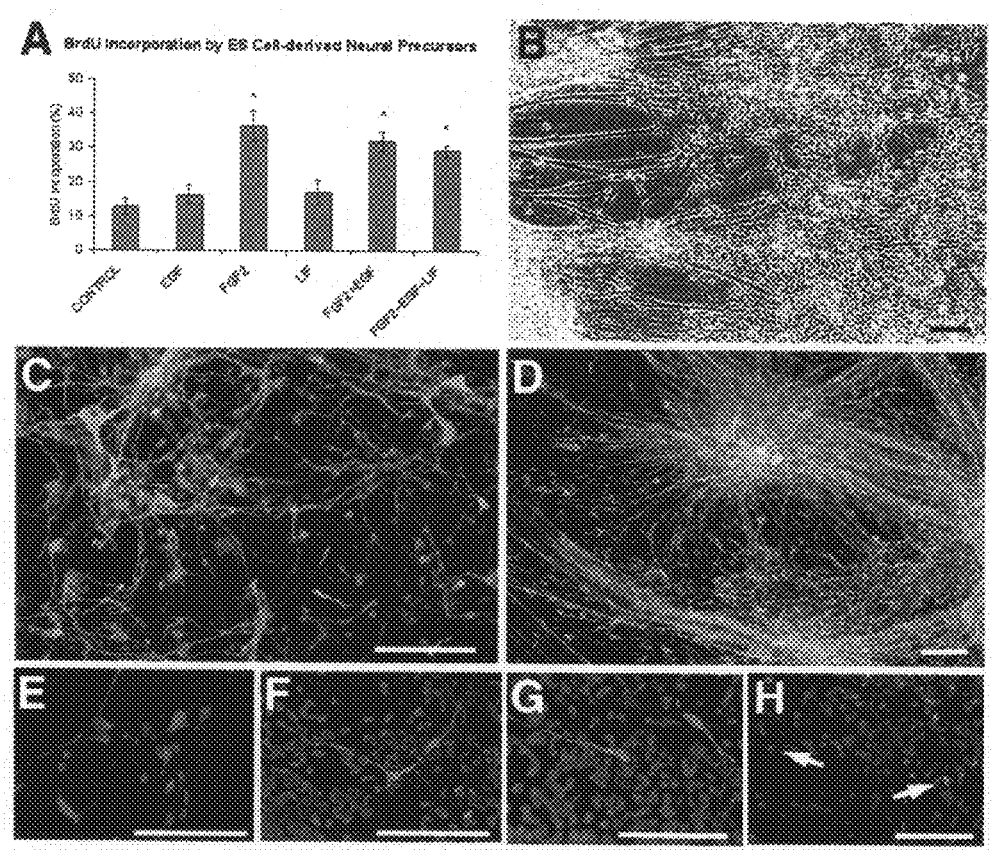

FIG. 2A-H. Characterization of ES cell-derived neural precursors in vitro. (FIG. 2A) BrdU incorporation by dissociated ES cell-derived neural precursors is elevated in the presence of FGF2 (20 ng/ml) but not with epidermal growth factor (EGF) (20 ng/ml) or leukemia inhibitory factor (LIF) (5 ng/ml). This is representative data from one of three replicate experiments. * indicates difference between the experimental group and the control group ($p<0.01$, n=4, student t-test). (FIG. 2B) Differentiation of a cluster of ES cell-derived neural precursors for three weeks shows neurite bundles with cells migrating along them. (FIG. 2C) Immunostaining after three weeks of differentiation indicates that the majority of cells are $\square_{II}$-tubulin$^+$ neurons (red) and that only a few cells are GFAP$^+$ astrocytes (green). (FIG. 2D) After forty-five days of differentiation, many more GFAP$^+$ astrocytes (green) appear along with NF200$^+$ neurites (red, yellowish due to overlapping with green GFAP). (FIG. 2E-G) ES cell-derived neurons with various morphologies express distinct neurotransmitters such as glutamate (FIG. 2E), GABA (FIG. 2F) and the enzyme tyrosine hydroxylase (FIG. 2G). O4$^+$ oligodendrocytes (arrows) are observed after two weeks of differentiation in a glial differentiation medium (FIG. 2H). Bar=100 μm FIG. 3A-K. Incorporation and differentiation of ES cell-derived neural precursors in vivo. Grafted cells are detected by in situ hybridization with a probe to the human alu-repeat element (FIG. 3A-E, G) or an antibody to a human-specific nuclear antigen (FIG. 3F). (FIG. 3A) Individual donor cells in the host cortex of an eight-week-old recipient (arrows). (FIG. 3B) Extensive incorporation of ES cell-derived neural precursors in the hippocampal formation. Cells hybridized with the human alu probe are labeled with red dots (pseudo-colored). (FIG. 3C) Incorporated human cells in the vicinity of the hippocampal pyramidal layer at P14. (FIG. 3D) ES cell-derived cells in the septum of a four-week-old recipient mouse. (FIG. 3E) High power view of an individual donor cell in the hypothalamus. Note the seamless integration between adjacent unlabeled host cells. (FIG. 3F) Donor cells in the striatum of a four-week-old host, detected with an antibody to a human-specific nuclear antigen. (FIG. 3G) Extensive migration of transplanted cells from the aqueduct into the dorsal midbrain. (FIG. 3H) Human ES cell-derived neuron in the cortex of a two-week-old host, exhibiting a polar morphology and long processes. The cell is double labeled with antibodies to a human-specific nuclear marker (green) and $\beta_{III}$-tubulin (red). (FIG. 3I) Network of donor-derived axons in the fimbria of the hippocampus, identified with an antibody to human neurofilament. (FIG. 3J) Donor-derived multipolar neuron, double labeled with an antibody recognizing the a and b isoforms of MAP2. (FIG. 3K) ES cell-derived astrocyte in the cortex of a four-week-old animal, double labeled with the human-specific nuclear marker (green) and an antibody to GFAP (red). Note that all the double labelings are confocal images and are confirmed by single optical cuts. Bars: FIG. 3A, FIG. 3B, FIG. 3G 200 μm; FIG. 3C, FIG. 3D 100 μm; FIG. 3E, FIG. 3F, FIG. 3H-K 10 μm.

Figure 4:
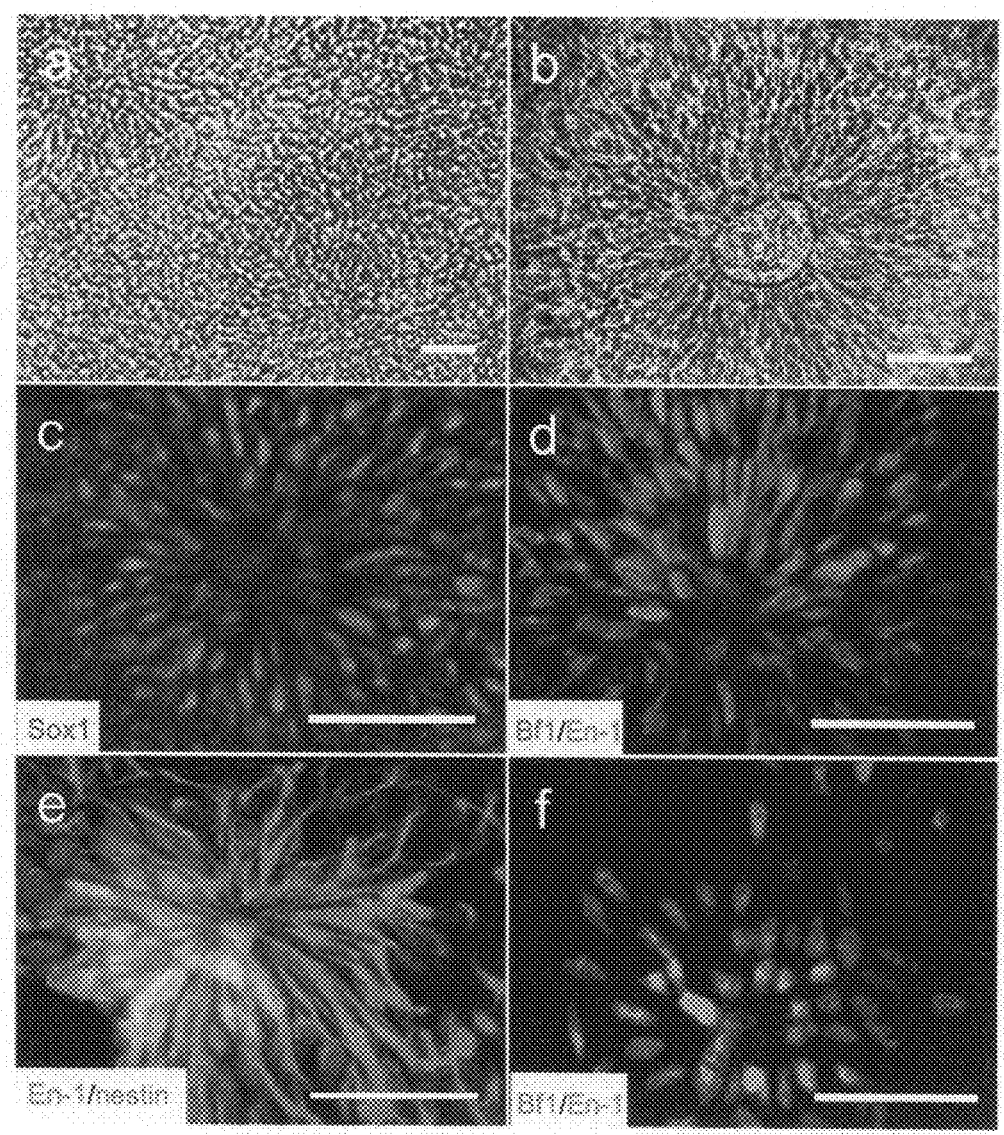

FIG. 4. Generation and regional specification of neuroectodermal cells. FIG. 4A. Columnar cells appeared in the differentiating ES cell colony at day nine in the presence of 20 ng/ml of FGF2. FIG. 4B. The columnar cells formed neural tube-like rosettes at day fourteen. FIG. 4C. The cells in the rosettes with columnar morphology were positive for Sox1 (red). FIG. 4D. The neural rosette cells in FGF2 treated cultures expressed Bf1 (red), but not En-1 (green). FIG. 4E. En-1 (green) expression was observed in the nestin$^+$ (red) neuroectodermal cells that were treated by six days with fibroblast growth factor 8 (FGF8) (100 ng/ml) at day nine, expanded in FGF8 for four days and then treated with sonic hedgehog (SHH) (200 ng/ml) for another six days on laminin substrate). FIG. 4F. These En-1$^+$ cells (green) were negative for Bf1 (red) in the culture treated as in FIG. 4E. The cell nuclei were stained with Hoechst (c, d; Blue). Bar=50 μm.

Figure 5:
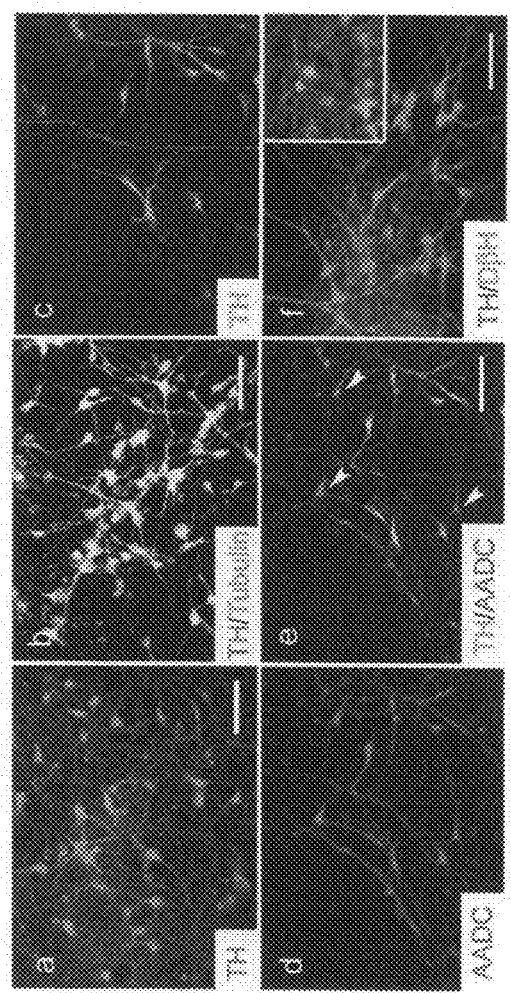

FIG. 5. Differentiation of DA neurons. FIG. 5A. About one third of the differentiated cells were tyrosine hydroxylase (TH) positive in the cultures that were treated with FGF8, SHH and ascorbic acid (AA) at three weeks of differentiation. FIG. 5B. All TH$^+$ cells (red) in the culture were positively stained with a neuronal maker $\beta_{III}$-tubulin (green). FIG. 5C-E. All TH$^+$ cells (d, green) in the culture were positively stained with aromatic acid decarboxylase (AADC) (d and e, red), but some AADC$^+$ cells were TH$^-$ (e, arrowheads). FIG. 5F. The TH$^+$ cells were negative for noradrenergic neuron marker dopamine β-hydroxylase (DβH) (green). The inset indicated that DβH positively stained cells in the section of adult rat brain stem. The cell nuclei were stained with Hoechst (a, b, f; Blue). Bar=50 μm.

Figure 6:
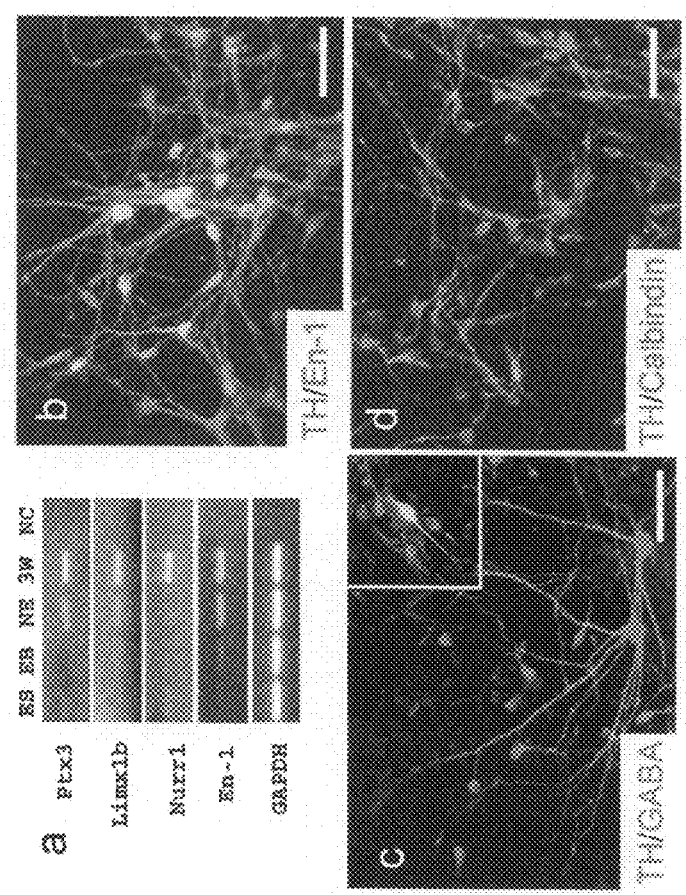

FIG. 6. Characterization of human ES cell-derived DA neurons. FIG. 6A. The differentiated DA neurons expressed genes characteristic of midbrain fate revealed by RT-PCR. EB: embryoid body; NE: neuroectodermal cells; 3w: the DA culture differentiated for three weeks; NC: negative control. FIG. 6B. The majority of TH$^+$ cells (red) in the cultures expressed midbrain marker En-1 (green). FIG. 6C. GABA expressing cells (red) were present in the culture but very few TH$^+$ cells (green) co-expressed GABA (red, inset). FIG. 6D. The TH$^+$ cells (red) were negative for calbindin (green). Bar=50 μm.

Figure 7:
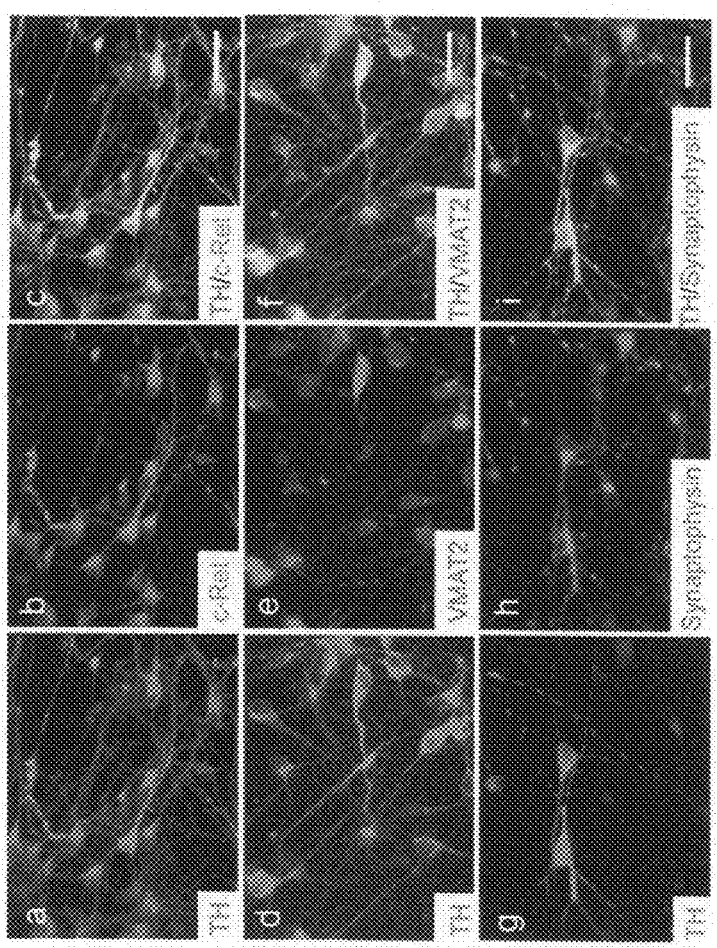

FIG. 7. Expression of receptors and transporters in the human ES cell-derived DA neurons. FIG. 7A-C. All TH$^+$ cells (a, green) expressed c-Ret (red). FIG. 7D-F. TH$^+$ cells (d, green) co-expressed VMAT2 (e and f; red). FIG. 7G-I. The TH$^+$ neurons (j, green) co-expressed synaptophysin (k and l, red). Bar=25 μm.

Figure 8:
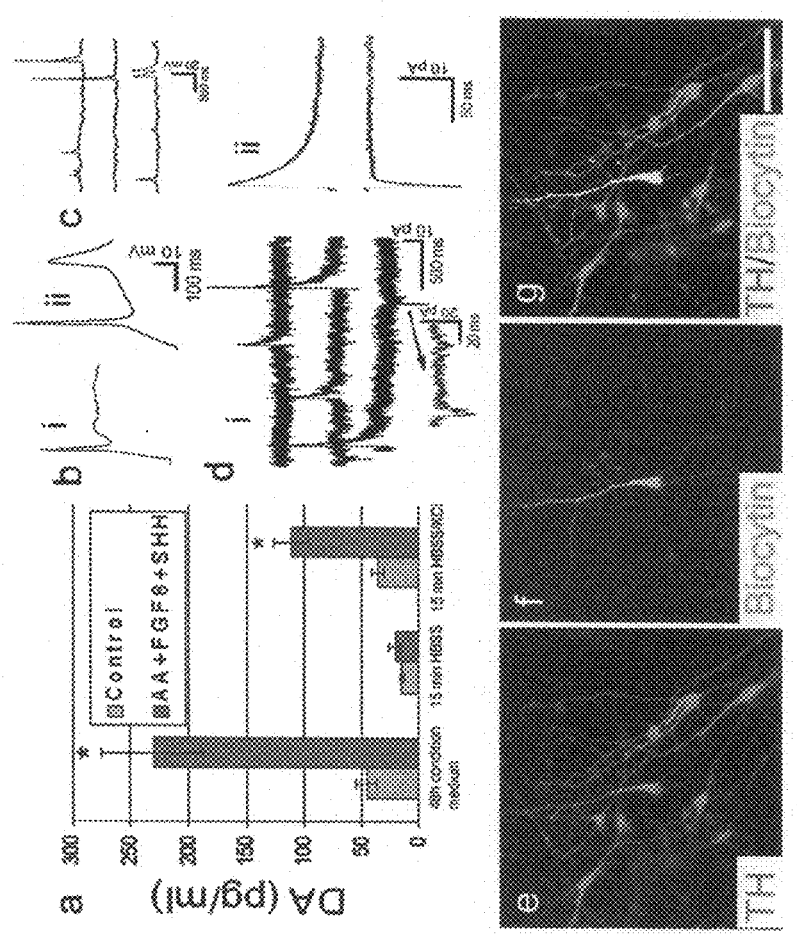

FIG. 8. Functional characteristics of the in vitro generated DA neurons. FIG. 8A. Spontaneous and depolarization (56 mM KCl in HBSS)-induced DA release in the control and the treated cultures at three weeks of differentiation. Data were presented as means ±SD from three experiments. *$p<0.05$ vs. control by the un-paired student t test. FIG. 8B. Action potentials evoked by depolarizing current steps (0.2 nA) in two neurons differentiated for thirty days. Passive membrane properties: (i) $V_{rest}$-49 mV, $C_m$ 15.5 pF, $R_m$ 5.0 GΩ; (ii) $V_{rest}$-72 mV, $C_m$ 45 pF, $R_m$ 885 GΩ. FIG. 8C. Spontaneous postsynaptic potentials in a neuron differentiated for thirty-six days. FIG. 8D. Spontaneous postsynaptic currents in a neuron maintained for thirty days in culture. The neuron was voltage clamped at −40 mV using a K-gluconate-based pipette solution. The outward currents reflect inhibitory events and inward currents reflect excitatory events in this low chloride recording solution. (ii) Averaged events from the cell illustrated in panel (i). The weighted decay time constants are 61.4 ms and 9.9 ms for inhibitory (n=17 events) and excitatory (n=14 events) currents. FIG. 8E-G. Immunostaining showed that the recorded neuron (f, green) was TH$^+$ (e and g, red). Bar=50 μm.

Figure 9:
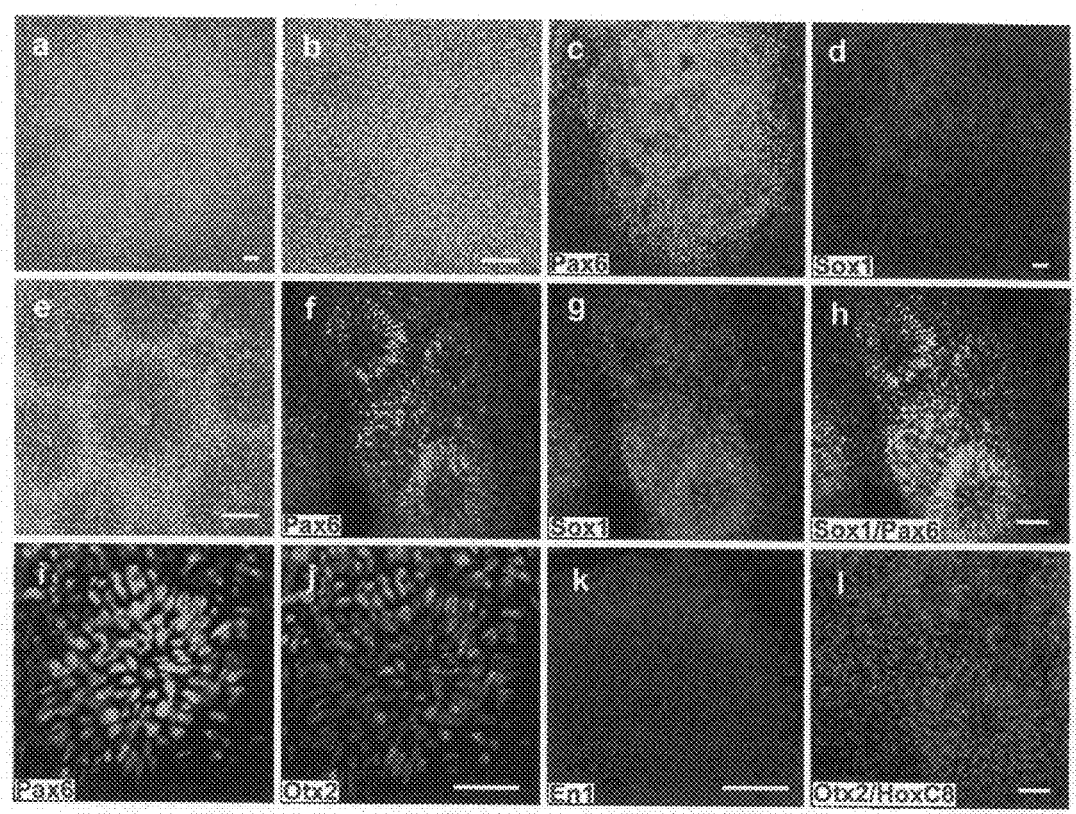

FIG. 9. Neuroectodermal cells induced by FGF2 display rostral phenotypes. ES cells, differentiated in FGF2 for ten days, displayed small, columnar morphology in the colony center, and organized into rosette formations (A,B). The columnar cells in the rosettes, but not the surrounding flat cells were positive for Pax6 and negative for Sox1 (C,D). By fourteen days, the columnar cells formed neural tube-like rosettes (E) and were positive for both Pax6 (F) and Sox1 (G,H). The Pax6+ cells (I) in the rosettes were also Otx2+ (J) but were En-1− (K). Cells in the neural tube-like rosettes were positive for Otx2 and negative for HoxC8 (L). Blue indicates Hoechst stained nuclei. Bar=50 μm.

Figure 10:
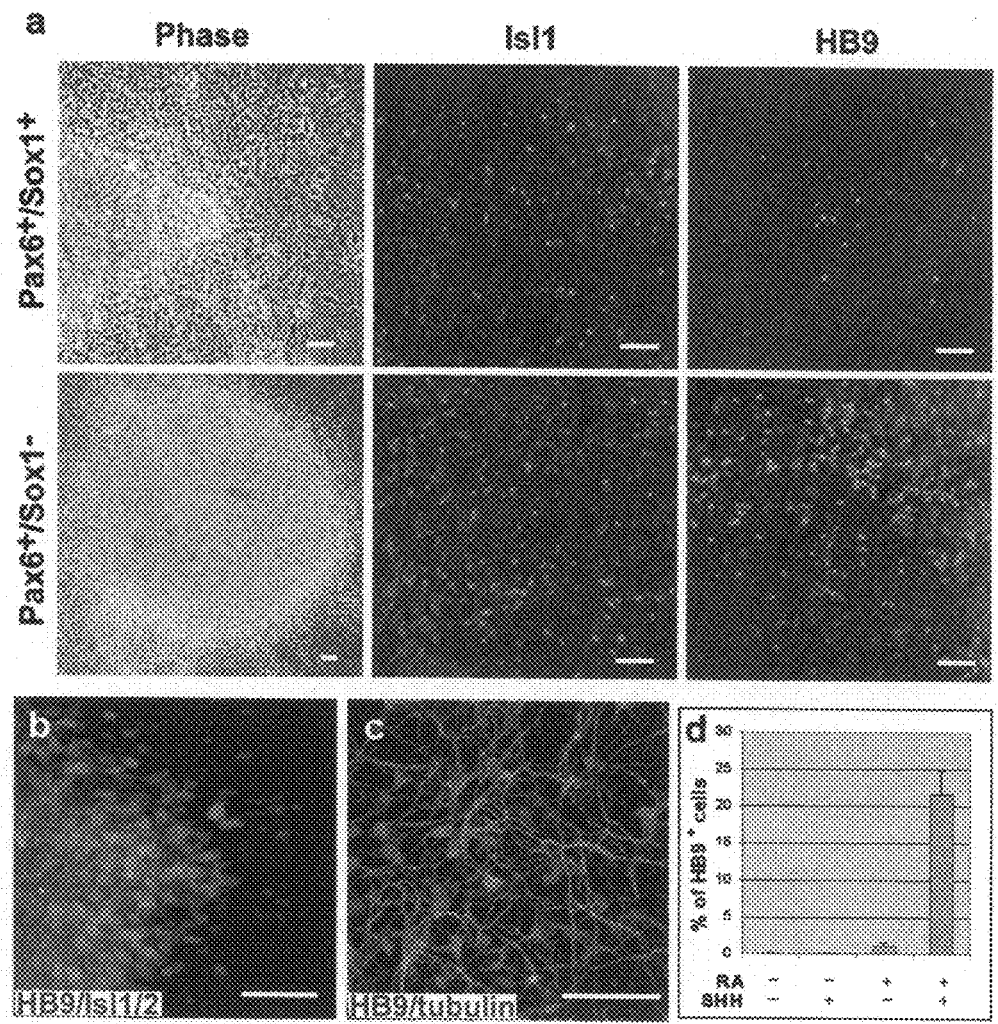

FIG. 10. Generation of motor neurons from neuroectodermal cells. (A) Differentiation of Sox1+ neuroectodermal cells for two weeks (upper row) revealed extensive neuronal generation in the outgrowth area, expression of Isl 1, but few HB9+ cells. Treatment of Pax6+/Sox1− neuroectodermal cells ($2^{nd}$ row) resulted in extensive neurite outgrowth with few migrating cells, expression of Isl 1, and a large proportion of HB9+ cells. About 50% Isl 1/2+ differentiated from early neuroectodermal cells were also HB9+ (B). HB9+ cells were also positive for $\beta_{III}$-tubulin (C). About 21% of the cells in the cluster were HB9+ when the cultures were differentiated in the presence of both retinoic acid (RA) and SHH, whereas few HB9+ cells were observed when cultured in either RA alone, or SHH alone, or neither (D). Blue indicates Hoechst stained nuclei. Bar=50 μm.

Figure 11:
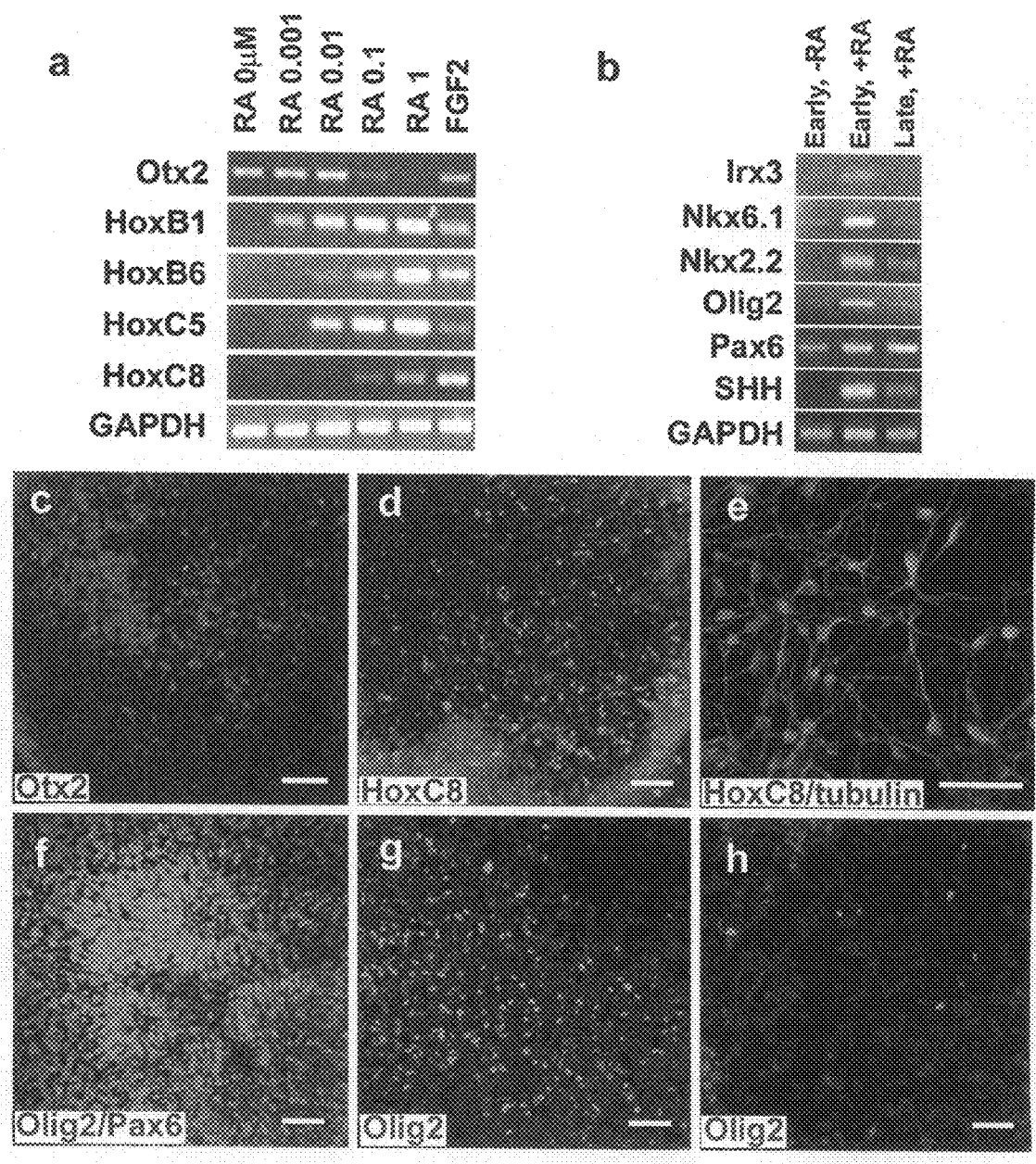

FIG. 11. Effect of RA, FGF2 and SHH on neuroectodermal cells. (A) RT-PCR analyses indicated changes of rostrocaudal genes from early rosettes cells that were cultured with RA or 20 ng/ml of FGF2 for one week in the neural induction medium. (B) Comparison of homeobox gene expression in early and late neuroectodermal cells treated with RA 0.1 μM for one week. The early neuroectodermal cells, treated with RA and then differentiated for twelve days, became mostly negative for Otx2 (C) but positive for HoxC8 (D). All the HoxC8+ cells were $\beta_{III}$-tubulin+ (E). The Pax6-expressing neuroectodermal cells were negative for Olig2 (F). After treatment with RA for one week and differentiation for two weeks in the presence of SHH (100 ng/ml), many cells expressed Olig2 (G). Few Olig2+ cells were observed when late neuroectodermal cells were treated with RA and then differentiated under the same culture condition (H). Blue indicates Hoechst stained nuclei. Bar=50 μm.

Figure 12:
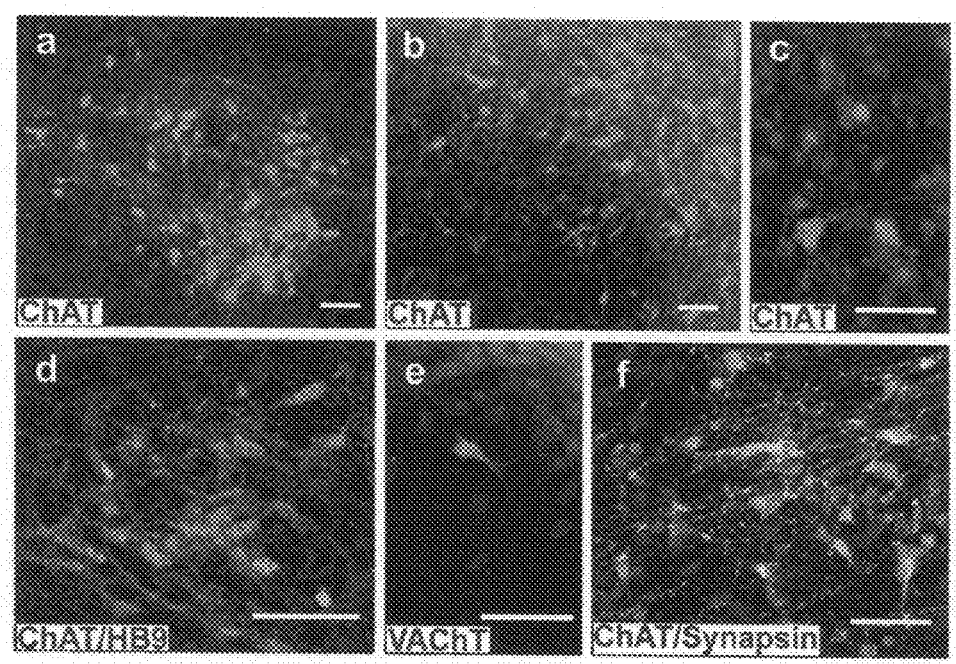

FIG. 12. Maturation of motor neurons in culture. ChAT-expressing cells were localized mainly in the cluster (A), and were large multipolar cells (B). Confocal image showed co-localization of ChAT in the soma and processes and HB9 in the nuclei in a three-week culture (C). Most cells in the cluster expressed VChAT (D). Many ChAT+ cells were also positive for synapsin in somas and processes after five weeks in culture (E).

Figure 13:
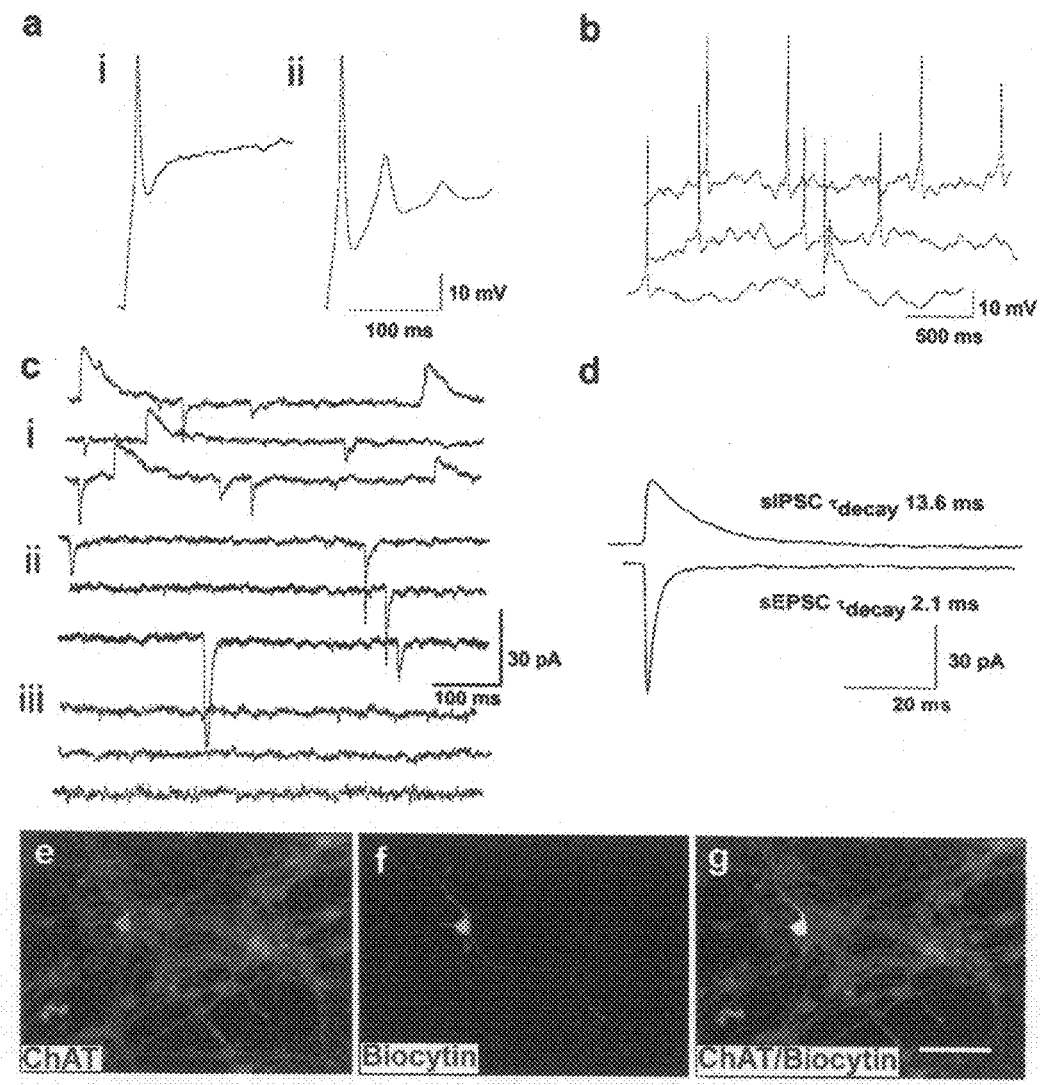

FIG. 13. Electrophysiological characterization of in vitro generated motoneurons. (A) AP's evoked by depolarizing current steps (0.15 nA) in neurons maintained for 42 DIV. Resting membrane potential (Vm)-59 mV (ai) and −70 mV (aii). (B) Spontaneous AP's in a neuron maintained for 42 DIV, Vm −50 mV. (C) Spontaneous inward and outward synaptic currents at −40 mV using K-gluconate-based pipette solution under control conditions (ci). Bath application of bicuculline (20 μM) and strychnine (5 μM) blocked outward currents (IPSCs, cii). Subsequent application of AP-5 (40 μM) and CNQX (20 μM) blocked the remaining inward currents (EPSCs, ciii). (D) Averaged sIPSCs and sEPSCs from the cell illustrated in panel c. (E-G) After recording, the coverslip cultures were immunostained with ChAT, showing that a biocytin-filled neuron was positive for ChAT. Bar=50 μm.

DETAILED DESCRIPTION OF THE INVENTION

Applicants herein disclose a method for generation of dopamine (forebrain and midbrain) and motor neurons from human embryonic stem cells. The preferred methods are generally described below and in Tables 1-3.

Specifically, Applicants disclose a method of differentiating early rosettes (Pax6+/Sox1−) from ES cells through an embryoid body intermediate. By differential treatment, Applicants can differentiate these early rosettes into three different forms of neural tube-like rosettes that are then suitable for development into forebrain dopamine neurons, midbrain dopamine neurons, or motor neurons.

TABLE 1

Generation of Dopamine and Motor Neurons from Human Embryonic Stem Cells

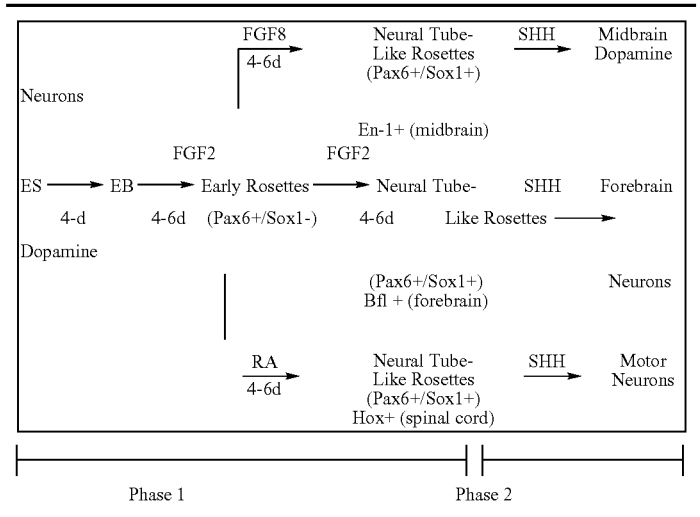

Applicants refer to Table 2 below, which describes Phases 1 and 2 for generating dopamine and motor neurons. Table 2 also describes various intermediate products that Applicants consider to be markers of suitable development.

TABLE 2

Generation of Dopamine and Motor Neurons from Human Embryonic Stem Cells

| | |
|---|---|
| Phase 1 | Propagation of embryonic stem cells and development of these cells into synchronized population of neural stem cells in the form of neural tube-like rosettes. |
| Phase 2 | Development of phase 1 cells through differential culture conditions into either forebrain dopamine neurons, midbrain dopamine neurons or motor neurons. |

As stated above, this invention includes two main embodiments. One embodiment is the procedure for generating a synchronized population of neural stem cells (or neuroepithelial cells) in the form of neural tube-like rosettes and expression of neuroepithelial markers Pax6, Sox1, nestin, Musashi-1. As used herein, "synchronize" means a population of cells that are at the same developmental stage, as opposed to those induced by RA which results in heterogeneous differentiation, i.e., the culture contains cells in developmental stages from progenitors to differentiated neurons. In the case here, we see either Pax6$^+$/Sox1$^-$ early neuroepithelial cells at an early stage or Pax6$^+$/Sox1$^+$ neuroepithelial cells at a later stage. In either stage, we do not see any differentiated neurons. This synchronized development will allow a directed differentiation toward a specialized neuronal fate, as described in this application.

The second embodiment is a method of further differentiation of the neuroepithelial cells to specialized neurons, such as midbrain dopamine neurons, forebrain dopamine neurons and spinal motor neurons.

Table 3 below, describes a preferred method of obtaining cells of the present invention. Table 3 includes both general culture broth components, that can be replaced by similar culture broths, and critical growth factor and timing components. When applicants refer to neural cell culture medium, many culture components are suitable. The sections below emphasize the culture components necessary for correct differentiation.

In general, a suitable medium is any medium used for growing neural cells. The following references (Bain, G., et al., supra, 1995; Okabe, S., et al., supra, 1996; Mujtaba, T., et al., supra, 1999; Brustle, O., et al., supra, 1999; Zhang, S.-C., et al., *J. Neurosci. Res.* 59:421-429, 2000; Zhang, S.-C., et al., *Proc. Natl. Acad. Sci. USA* 96:4089-4094, 1999; Svendsen, C. N., et al., *Exp. Neurol.* 137:376-388, 1996; Carpenter, M. K., et al., *Exp. Neurol.* 158:265-278, 1999; Vescovi, A. L., et al., *Exp. Neurol.* 156:71-83, 1999) use the same or similar medias.

1. Differentiation of Neuroepithelial Cells (Neural Stem Cells) from Human ES Cells The generation of neuroepithelial cells involves formation of embryoid bodies in suspension culture for 4-6 days, followed by adherent culture in the presence of growth factors, preferably FGF2 or FGF8, for 4-5 days when cells in the center of each colony become columnar and organize into a rosette form (FIG. 1A, FIG. 4A, FIG. 9A, B). (See Zhang, et al., *Nature Biotechnol.*, 2001) FGF4 and FGF9 are also suitable growth factors.

The columnar cells in these rosettes express a neural transcription factor Pax6 but do not express another neural transcription factor Sox1 (FIG. 9C, D). We call these rosettes "early rosettes" because they appear early and form by monolayer of columnar cells without a lumen. Every single colony possesses early rosettes. The total population of early rosette cells is at least 70% of the total cells.

Further culture of these early rosettes for 4-6 days will lead to formation of neural tube-like rosettes (FIG. 1B, FIG. 4B, FIG. 9E). The neural tube-like rosettes are formed by multiple layers of columnar cells with a clear lumen. The cells in the rosettes express Sox1 in addition to Pax6 (FIG. 4C, FIG. 9 F, G, H). The progression from early rosettes to neural tube-like rosettes takes about 4-6 days under our serum-free culture condition in the presence of FGF2, FGF4, FGF8, FGF9 at 10-20 ng/ml or RA at 0.001-1 µM.

The process of neuroepithelial differentiation, from ES cells to formation of neural tube-like rosettes, takes 14-16 days. Human ES cells are derived from a 5.5 day-old human embryo (Thomson, J. A., et al., supra, 1998). Hence, the development of neuroepithelial cells from human ES cells in our culture system compares well to the 19-21 days the development takes in a human embryo. In normal human development, neural tube forms at 20-21 days. Thus, neuroepithelial differentiation from human ES cells mirrors normal human embryo development (Zhang, S. C., *J. Hematother. Stem Cell Res.* 12:625-634, 2003).

The two-stage neuroepithelial development, as evidenced by morphological transformation and clear-cut gene expression patterns has not been described before. Pax6 and Sox1 have been shown to be expressed by neuroepithelial cells when neural tube forms at the same time in frogs, zebrafish, chicks, and mice (Pevny, et al., *Development* 125:1967-1978, 1998). Hence, we believe the finding of sequential Pax6 and Sox1 expression along neuroepithelial differentiation in human ES cells is novel and may be unique to humans. The Pax6+/Sox1– neuroepithelial cells represent the earliest neuroepithelial cells thus far identified. The functional significance of these cells is relevant to the present invention in that the Pax6+/Sox1– neuroepithelial cells in the early rosettes, but not the Pax6+/Sox1+ neuroepithelial cells in the neural tube-like rosettes, can be efficiently induced to become neurons carrying positional identities other than forebrain such as midbrain dopamine neurons and spinal motor neurons (Table 1, see above).

Every differentiating ES cell colony forms neural tube-like rosettes. The neuroepithelial cells represent at least 70-90% of the total differentiated cells.

The neuroepithelial cells in the form of neural tube-like rosettes can be purified through treatment with a low concentration of dispase and differential adhesion (described in U.S. Ser. No. 09/960,382).

2. Generation of Midbrain Dopamine Neurons

A functional neuron with potential therapeutic application must possess at least two additional characteristics in addition to being a neuron: a specific positional identity and the capacity to synthesize, release, and uptake a neural transmitter.

The first step in generating midbrain dopamine neurons is the induction of a midbrain identity. Treatment of the Pax6+/Sox1− early rosette cells, but not the Pax6+/Sox1+ neural tube-like rosette cells, with FGF8 (50-200 ng/ml) for 6-7 days results in efficient differentiation of the cells to progenitors that express midbrain transcription factors Engrailed 1 (En-1) and Pax 2 (FIG. 4E, F) and down regulation of forebrain marker Bf-1 (FIG. 4D).

The second step is to culture the midbrain progenitors in the presence of sonic hedgehog (SHH, 50-250 ng/ml) for 6-7 days, then in the regular neuronal differentiation medium (such as that described in Table 3) for additional 2 weeks until dopamine neurons develop. Preferably, at least 35% of the total differentiated cells will become dopamine neurons.

A preferred differentiation medium is described in Table 3.

The dopamine neurons express TH, AADC, but not DbH and PNMT (FIG. 5) enabling the synthesis of dopamine but not the further metabolism to norepinephrine or nephrine.

The dopamine neurons express En-1, ptx3, Nurr1, and Lmx1b (FIG. 6A, B), transcription factors that are required for midbrain dopamine neuron development.

The dopamine neurons do not express GABA (FIG. 6C). Coexpression with GABA is the feature of dopamine neurons in the olfactory bulb.

The dopamine neurons do not express calbindin (FIG. 6D). Coexpression with calbindin is the feature of dopamine neurons in the tegamental area of the midbrain.

Together, the above features indicate that the dopamine neurons generated in our culture system are midbrain dopamine neurons, more closely resembling those in the substantial nigra, the dopamine neurons that are lost in Parkinson's disease.

The dopamine neurons possess c-ret, a receptor for GDNF (FIG. 7A, B, C), a growth factor required for survival and function of dopamine neurons.

The dopamine neurons also express VMAT2 (FIG. 7D, E, F), a transporter required for storage and release dopamine. They also express DAT (FIG. 7G, H, I), a transporter necessary for dopamine uptake after release. Thus, the dopamine neurons generated in our culture system possess necessary machinery for synthesis, storage, release, and uptake of the transmitter dopamine.

The dopamine neurons express synaptophysin (FIG. 7) for formation of synapses. They can fire action potentials and can secrete dopamine in response to stimulation (FIG. 8). Therefore, the dopamine neurons are functional.

3. Generation of Spinal Motor Neurons

The first step in generating spinal motor neurons is the induction of a spinal cord (caudal) identity. Treatment of the Pax6+/Sox1− early rosette cells, but not the Pax6+/Sox1+ neural tube-like rosette cells (FIG. 10A), with RA (0.001-1 uM) for 6-7 days results in efficient differentiation of the cells to progenitors that express spinal cord transcription factor Hox genes such as HoxB1, HoxB6, HoxC5, HoxC8, but not forebrain markers Otx2 and Bf-1 or midbrain marker En-1 (FIG. 11A, C, D, E)

The second step is to culture the spinal cord progenitors in the presence of sonic hedgehog (SHH, 50-250 ng/ml) for 6-7 days to induce a ventralized progenitor character, as evidenced by expression of Olig2, (FIG. 11F, G, H), a transcription factor expressed by only ventral neural progenitors, then in the regular neuronal differentiation medium for additional 7-10 days until spinal motor neurons develop.

A preferred differentiation medium is described in Table 3.

In a preferred embodiment, at least 22% of the total differentiated cells become spinal motor neurons. The motor neurons express HB9, islet1/2, and Lim3 (FIG. 10), transcription factors that are specifically expressed by spinal cord motor neurons. The motor neurons also express HoxB1, HoxB6, HoxC5, HoxC8, but not forebrain markers Otx2 and Bf-1 or midbrain marker En-1 (FIG. 11A, C, D, E), indicating that they are spinal motor neurons.

The motor neurons express CHAT (FIG. 12A, B, C, D), an enzyme necessary for synthesizing the motor neuron transmitter acetylcholine. The motor neurons also express VAChT (FIG. 12E), suggesting that the motor neuron can store and uptake the transmitter acetylcholine.

In addition, the motor neurons express synapsin (FIG. 12F) for formation of synapses. They can fire action potentials (FIG. 13). Therefore, the motor neurons are functional. We have data showing that the motor neurons release acetycholine, as analyzed by HPLC.

4. Generation of Forebrain Neurons

In another embodiment, the present invention is a method of differentiating primate ES cells (preferably human ES cells) into forebrain dopamine neurons, preferably transplantable neural precursors suitable for nervous system repair. One would preferably begin the method as described above for mid-brain dopamine neuron generation. To generate forebrain neurons, the Pax6+/Sox1− cells are treated for an additional 4-6 days with FGF2 and are then treated with SHH. The steps in generating forebrain dopamine neurons and the analyses for determining the dopamine neuron characters are similar to those described for midbrain dopamine neurons. The main difference is the use of morphogens at a particular period and the features of dopamine neurons.

The first step in generating forebrain dopamine neurons is the induction of a midbrain identity. Treatment of the Pax6+/Sox1− early rosette cells with FGF2 (10-20 ng/ml) for 6-7 days results in efficient differentiation of the cells to progenitors that express forebrain transcription factors Bf-1 and Otx2.

The second step is to culture the forebrain progenitors in the presence of sonic hedgehog (SHH, 50-250 ng/ml) for 6-7 days, then in the regular neuronal differentiation medium for additional 2 weeks until dopamine neurons develop. 35% of the total differentiated cells become dopamine neurons. The description below, taken from U.S. patent application Ser. No. 09/970,382, describes a preferred method.

A primate ES cell line, preferably a human ES cell line, is first obtained and propagated. One may obtain an ES cell line as described in Thomson, J. A., et al., Science 282:1145-1147 (1998) and U.S. Pat. Nos. 5,843,780 and 6,200,806 or by other methods suitable to obtain a ES cell line with normal karyotypes and the ability to proliferate in an undifferentiated state after continuous culture for at least eleven months and preferably twelve months. The embryonic stem cell line will also retain the ability, throughout the culture, to form trophoblasts and to differentiate into tissue derived from all three embryonic germ layers (endoderm, mesoderm and ectoderm).

The cells are then cultured. In a preferred embodiment of the present invention, the cells are propagated on a feeder layer of irradiated mammalian, preferably mouse, embryonic fibroblasts, preferably as disclosed below and in Thomson, J. A., et al., supra, 1998 and U.S. Pat. Nos. 5,843,780 and 6,200,806. We also envision that the cells may be propagated without feeder cell layers.

The ES cell colonies are typically removed intact from adherent cultures by treatment with dispase and grown in a suspension as free-floating ES cell aggregates called embryoid bodies (EBs), preferably for four days as described below.

The EBs are then cultured in medium containing FGF2, preferably at 20 ng/ml, to generate early rosette cells. The other preferred components of the medium are as described in Table 3. However, many other medium components are suitable. In general, a suitable medium is any medium used for growing neural cells. The following references (Bain, G., et al., supra, 1995; Okabe, S., et al., supra, 1996; Mujtaba, T., et al., supra, 1999; Brustle, O., et al., supra, 1999; Zhang, S.-C., et al., *J. Neurosci. Res.* 59:421-429, 2000; Zhang, S.-C., et al., *Proc. Natl. Acad. Sci. USA* 96:4089-4094, 1999; Svendsen, C. N., et al., *Exp. Neurol.* 137:376-388, 1996; Carpenter, M. K., et al., *Exp. Neurol.* 158:265-278, 1999; Vescovi, A. L., et al., *Exp. Neurol.* 156:71-83, 1999) use the same or similar medium.

After approximately five days of culture in the medium, the plated EBs will generate an outgrowth of flattened cells and by seven days the center small elongated cells will generate rosette formations such as seen in FIG. 1B. These formations resemble the early neural tube (insert of FIG. 1B). One may confirm the presence of neural precursors by morphology or by immunofluorescence analysis using neural marker antigens such as nestin and Musashi I, as described below. Preferably, the neural precursors comprise at least 72%, and most preferably at least 84%, of the total cells.

One may wish to further isolate the neural tube-like rosettes, preferably by differential enzymatic treatment and adhesion, as described below in the Examples. In brief, treatment with dispase will lead to the preferential detachment of the central neuroepithelial islands. To separate the clusters of rosette cells from the surrounding flat cells, the differentiating EBs cultured for eight to ten days are preferably incubated with 0.1-0.2 mg/ml dispase (Gibco BRL, Lifetechnologies, Rockville, Md.) at 37° C. for 15-20 minutes. Alternatively, 0.2 mg/ml of dispase may be used. The rosette clumps retract whereas the surrounding flat cells remain adherent. At this point, the rosette clumps may be dislodged by swaying the flask, which leaves the flat cells adherent. The clumps are pelleted, gently triturated with a 5 ml pipette and plated into a culture flask for 30 minutes to allow the contaminating individual cells to adhere. The floating rosette clumps are then transferred to a new flask, preferably coated with poly-(2-hydroxyethyl-methacrylate) to prohibit attachment, and cultured in a medium used for human neural precursors with the presence of FGF2 (typically 20 ng/ml). As described below in the Examples, treatment with dispase followed by differential adhesion will yield a highly enriched population of neural precursor cells, typically at least 90% and most preferably at least 96%. Additionally, one may use other methods, such as immune separation using an antibody to PSA-NCAM, to separate the neural precursor cells.

The Examples below demonstrate the human ES cell-derived neural precursors can generate all three CNS cell-types in vitro.

The table below is a flow chart of various aspects of this embodiment of the present invention:

TABLE 4

Characterization of the Neural Precursor Cells in vitro and in vivo

| | |
|---|---|
| ES cells | |
| ⇓ | Treatment with dispase and cultured in free-floating condition with ES medium without FGF2 for 4 days followed by chemically defined medium with FGF2 (10-20 ng/ml) for 2 days. |
| Embryoid Bodies | |
| ⇓ | Adherent culture in a chemically defined medium containing FGF2 for 7-9 days. |
| Differentiation to Neural tube-like structures | |
| ⇓ | These are unique structures representative of neural epithelial cells as defined by histology and immunohistochemistry. Neural precursor cells typically comprise at least 72~84% of the total cells. Treatment with dispase followed by differential adhesion yields a highly enriched population of neural precursor cells (preferably at least 95%). |
| Isolation of Neural Precursor Cells with Dispase Treatment | |

In another embodiment, the present invention is a cell population comprising at least 72%, and preferably 84%, neural precursor cells. These neural precursor cells can be defined by being nestin and Musashi I positive. FIG. 1B illustrates the rosette formation characterizing these cells. By rosette formation, we mean that cells are columnar in shape and are arranged in a tubular (rosette) structure, resembling the neural tube (developing brain) in the body. The columnar cell morphology and tubular structures are shown in the insert of FIG. 1B.

In another embodiment, the present invention is a cell population of at least 90% and preferably at least 96% neural precursor cells. One would preferably obtain these cells after differential enzymatic treatment and adhesion, as described below in the Examples.

5. Use of Cell Populations of the Present Invention

Generation of specialized human neuronal cell types with specific transmitter phenotypes and unique positional identities provide a source of transplantable cells for treatment in neurological disorders, such as midbrain dopamine neurons for Parkinson's disease, forebrain dopamine neurons for psychological diseases, spinal motor neurons for spinal cord injury and motor neuron diseases including ALS.

Establishment of stepwise and chemically defined culture systems for directed differentiation of human embryonic stem cells first to neuroepithelial cells and then to specialized neurons also offers an unprecedented system for screening toxic and therapeutic agents. At the present, toxicological and therapeutic drug screenings are performed using animals, animal cell cultures, or genetically abnormal human cell lines. Human embryonic stem cells and their differentiation to specialized neuronal cells represent a normal process of human neural development. Hence, the invention described herein will be amenable to screen agents that affect normal human neural development or those that potentially result in abnormal brain development, as well as those that may stimulate regeneration of the neuronal types in diseased conditions. In addition, the described system can be readily modified to mimic pathological processes that lead to death of dopamine neurons (such as in Parkinson's disease) or motor neurons (such as in ALS), which may be effectively used to screen therapeutic agents that are designed to treat these diseases.

In a preferred method of this embodiment of the present invention, one would expose one of the cell populations of the present invention to a test compound and compare the results of such exposure to a control cell population that has not been exposed. One could understand whether a particular test compound affected the cell population by examining characteristics of the culture and comparing them to known developmental characteristics contained within the present application.

TABLE 3A

Neuroepithelial (Neural Stem) Cells - Preferred Culture Conditions and Markers

| Phase | Cell Name | Cell-Specific Marker | Culture Media Constituents | Culture Media Conditions | Electro-physiological Markers |
|---|---|---|---|---|---|
| Phase 1 | ES | Oct4+, SSEA4+ Pax6−, Sox1− | Irradiated mouse fibroblast; DMDM/F12 (1:1); 20% serum replacer; 2 µg/ml heparin; 0.1 mM β-mercaptoethanol; 4 ng/ml FGF2 | media changed every day; 36.5° C., 5% $CO_2$ | N/A |
| Phase 1 | $1^{st}$ Dispase Treatment | N/A | 1-2 mg/ml dispase | 30 minutes; 37° C.; ambient atmosphere | N/A |
| Phase 1 | EB | Oct4+, SSEA4+ Pax 6−, Sox 1− | Suspension culture, no mouse fibroblast; DMDM/F12 (1:1); 20% serum replacer; 2 µg/ml heparin; 0.1 mM β-mercaptoethanol; NO FGF2 | 4 days; media changed every day; 25-$cm^2$ tissue culture flask; 36.5° C., 5% $CO_2$ | N/A |
| Phase 1 | EB | Oct4+, SSEA4+ Pax 6−Sox 1− | Suspension culture, no mouse fibroblast; DMEM/F12 (1:1); 25 µg/ml insulin; 100 µg/ml transferrin; 20 nM progesterone; 60 µM putrescine; 30 nM sodium selenite; 10-20 ng/ml FGF2 | 2 days; media changed every day; 25-$cm^2$ tissue culture flask; 36.5° C., 5% $CO_2$ | N/A |
| Phase 1 | Early Rosettes | Oct4−, SSEA4− Pax 6+, Sox 1− nestin+ PSA-NCAM− | DMEM/F12 (1:1); 25 µg/ml insulin; 100 µg/ml transferrin; 20 nM progesterone; 60 µM putrescine; 30 nM sodium selenite; 10-20 ng/ml FGF2 | 5 days; media changed every 2 days; 25-$cm^2$ tissue culture flask; 36.5° C., 5% $CO_2$ | N/A |
| Phase 1 | Neural-like Tube Rosettes | Pax 6+, Sox 1+ Nestin+, Bf-1+ | DMEM/F12 (1:1); 25 µg/ml insulin; 100 µg/ml transferrin; 20 nM progesterone; 60 µM putrescine; 30 nM sodium selenite; 10-20 ng/ml FGF2 | 3-5 days; media changed every 2 days; 25-$cm^2$ tissue culture flask; 36.5° C., 5% $CO_2$ | N/A |
| Phase 1 | $2^{nd}$ Dispase Treatment | N/A | 0.1-0.2 mg/ml dispase | 15-20 minutes; 36.5° C.; ambient atmosphere | N/A |

TABLE 3B

Midbrain Dopamine Neurons - Preferred Culture Conditions and Markers

| Phase | Cell Name | Cell-Specific Marker | Culture Media Constituents | Culture Media Conditions | Electro-physiological Markers |
|---|---|---|---|---|---|
| Phase 1 | ES | Oct4+, SSEA4+ Pax6−, Sox1− | Irradiated mouse fibroblast; DMDM/F12 (1:1); 20% serum replacer; 2 µg/ml heparin; 0.1 mM β-mercaptoethanol; 4 ng/ml FGF2 | media changed every day; 36.5° C., 5% $CO_2$ | N/A |
| Phase 1 | ES ($1^{st}$ Dispase Treatment) | N/A | 1-2 mg/ml dispase | 30 minutes; 37° C.; ambient atmosphere | N/A |
| Phase 1 | EB | Oct4+, SSEA4+ Pax 6−Sox1− | Suspension culture, no mouse fibroblast; DMDM/F12 (1:1); 20% serum replacer; 2 µg/ml heparin; 0.1 mM β-mercaptoethanol; NO FGF2 | 4 days; media changed every day; 25-$cm^2$ tissue culture flask; 36.5° C., 5% $CO_2$ | N/A |
| Phase 1 | EB | Oct4+, SSEA4+ Pax 6−Sox 1− | Suspension culture, no mouse fibroblast; DMEM/F12 (1:1); N2 supplement; 2 ng/ml heparin; 10-20 ng/ml FGF2 | 2 days; media changed every day; 25-$cm^2$ tissue culture flask; 36.5° C., 5% $CO_2$ | N/A |
| Phase 1 | Early Rosettes | Oct4−, SSEA4− Pax 6+, Sox 1− nestin+ PSA-NCAM− | DMEM/F12 (1:1); N2 supplement; 2 ng/ml heparin, 10-20 ng/ml FGF2 | 5 days; media changed every 2 days; 25-$cm^2$ tissue culture flask; 36.5° C., 5% $CO_2$ | N/A |
| Phase 2 | Neural-like Tube Rosettes | Pax 6+, Sox 1+ Nestin+, En1+, Pax2+ | DMEM/F12 (1:1); N2 supplement; 2 ng/ml heparin; 10-200 ng/ml FGF8 | 5-6 days; media changed every 2 days; 25-$cm^2$ tissue culture flask; 36.5° C., 5% $CO_2$ | N/A |
| Phase 2 | Neural epithelial cells ($2^{nd}$ Dispase Treatment) | N/A | 0.1-0.2 mg/ml dispase | 15-20 minutes; 36.5° C.; ambient atmosphere | N/A |
| Phase 2 | Expansion of neuro-epithelial cells | Pax 6+, Sox 1+ Nestin+, En1+, Pax2+ | DMEM/F12 (1:1); N2 supplement; 2 ng/ml heparin; 10-200 ng/ml FGF8 +50-250 ng/ml SHH | 5-6 days; media changed every 2 days; 25-$cm^2$ tissue culture flask; 36.5° C., 5% $CO_2$ | N/A |

TABLE 3B-continued

Midbrain Dopamine Neurons - Preferred Culture Conditions and Markers

| Phase | Cell Name | Cell-Specific Marker | Culture Media Constituents | Culture Media Conditions | Electro-physio-logical Markers |
|---|---|---|---|---|---|
| Phase 2 | 1st dissociation | N/A | N/A | Accutase (Gibco) | N//A |
| Phase 2 | Midbrain DA neurons | TH+, AADC+, DbH−, PNMT−, En1+, Bf-1−, Nurr1+, ptx3+, Lmx1b+, VMAT+, DAT+, c-ret+, GABA−, Calbindin−, CCK−, | Neurobasal medium; N2; 0.1 mM non-essential amino acids; 0.5 mM glutamine; 1 µg/ml laminin; 1 µM cAMP; 200 µM ascorbic acid; 10 ng/ml BDGF; 10 ng/ml GDNF | 2-3 weeks; media changed every 2 days; culture Petri dishes; 36.5° C., 5% $CO_2$ | Secretion of DA, Action potentials. |

TABLE 3C

Spinal Motor Neurons - Preferred Culture Conditions and Markers

| Phase | Cell Name | Cell-Specific Marker | Culture Media Constituents | Culture Media Conditions | Electro-physio-logical Markers |
|---|---|---|---|---|---|
| Phase 1 | ES | Oct4+, SSEA4+ Pax6−, Sox1− | Irradiated mouse fibroblast; DMDM/F12 (1:1); 20% serum replacer; 2 µg/ml heparin; 0.1 mM β-mercaptoethanol; 4 ng/ml FGF2 | media changed every day; 36.5° C., 5% $CO_2$ | N/A |
| Phase 1 | ES (1st Dispase Treatment) | N/A | 1-2 mg/ml dispase | 30 minutes; 37° C.; ambient atmosphere | N/A |
| Phase 1 | EB | Oct4+, SSEA4+ Pax 6−, Sox 1− | Suspension culture, no mouse fibroblast; DMDM/F12 (1:1); 20% serum replacer; 2 µg/ml heparin; 0.1 mM β-mercaptoethanol; NO FGF2 | 4 days; media changed every day; 25-cm$^2$ tissue culture flask; 36.5° C., 5% $CO_2$ | N/A |
| Phase 1 | EB | Oct4+, SSEA4+ Pax 6−, Sox 1− | Suspension culture, no mouse fibroblast; DMEM/F12 (1:1); N2 supplement; 2 ng/ml heparin; 10-20 ng/ml FGF2 | 2 days; media changed every day; 25-cm$^2$ tissue culture flask; 36.5° C., 5% $CO_2$ | N/A |
| Phase 1 | Early Rosettes | Oct4−, SSEA4− Pax 6+, Sox 1− nestin+ PSA-NCAM− | DMEM/F12 (1:1); N2 supplement; 2 ng/ml heparin, 0.01-1 M RA | 5 days; media changed every 2 days; 25-cm$^2$ tissue culture flask; 36.5° C., 5% $CO_2$ | N/A |
| Phase 2 | Neural-like Tube Rosettes | Pax 6+, Sox 1+ Nestin+, HoxC+, HoxB+, Olig2+, Otx2−, Bf1−, En1− | DMEM/F12 (1:1); N2 supplement; 2 ng/ml heparin; 0.01-1 M RA; 10-500 ng/ml SHH | 5-6 days; media changed every 2 days; 25-cm$^2$ tissue culture flask; 36.5° C., 5% $CO_2$ | N/A |
| Phase 2 | Neural epithelial cells (2nd Dispase Treatment) | N/A | 0.1-0.2 mg/ml dispase | 15-20 minutes; 37° C.; ambient atmosphere | N/A |
| Phase 2 | Expansion of neuro-epithelial cells | Pax 6+, Sox 1+ Nestin+, HoxC+, HoxB+, Olig2+, Otx2−, Bf1−, En1− | DMEM/F12 (1:1); N2 supplement, 2 ng/ml heparin; 0.01-1 M RA +50-250 ng/ml SHH + 10 ng/ml FGF2. | 5-6 days; media changed every 2 days; 25-cm$^2$ tissue culture flask; 36.5° C., 5% $CO_2$ | N/A |
| Phase 2 | 1st dissociation | N/A | N/A | Accutase (Gibco) | N//A |
| Phase 2 | Spinal Motor neurons | HB9+, Islet+, Lim3+, HoxC+, ChAT+, VAChAT+, | Neurobasal medium; N2; 0.1 mM non-essential amino acids; 0.5 mM glutamine; 1 µg/ml laminin; 50 ng/ml SHH; 10 ng/ml BDNF, 10 ng/ml GDNF, 10 ng/ml IGF1 | 2-3 weeks; media changed every 2 days; culture Petri dishes; 36.5° C., 5% $CO_2$ | Action potentials. |

TABLE 3D

Forebrain Dopamine Neurons - Preferred Culture Conditions and Markers

| Phase | Cell Name | Cell-Specific Marker | Culture Media Constituents | Culture Media Conditions | Electrophysiological Markers |
|---|---|---|---|---|---|
| Phase 1 | ES | Oct4+, SSEA4+ Pax6−, Sox1− | Irradiated mouse fibroblast; DMDM/F12 (1:1); 20% serum replacer; 2 µg/ml heparin; 0.1 mM β-mercaptoethanol; 4 ng/ml FGF2 | media changed every day; 36.5° C., 5% $CO_2$ | N/A |
| Phase 1 | ES (1st Dispase Treatment) | N/A | 1-2 mg/ml dispase | 30 minutes; 37° C.; ambient atmosphere | N/A |
| Phase 1 | EB | Oct4+, SSEA4+ Pax 6−Sox 1− | Suspension culture, no mouse fibroblast; DMDM/F12 (1:1); 20% serum replacer; 2 µg/ml heparin; 0.1 mM β-mercaptoethanol; NO FGF2 | 4 days; media changed every day; 25-$cm^2$ tissue culture flask; 36.5° C., 5% $CO_2$ | N/A |
| Phase 1 | EB | Oct4+, SSEA4+ Pax 6−Sox 1− | Suspension culture, no mouse fibroblast; DMEM/F12 (1:1); N2 supplement; 2 ng/ml heparin; 10-20 ng/ml FGF2 | 2 days; media changed every day; 25-$cm^2$ tissue culture flask; 36.5° C., 5% $CO_2$ | N/A |
| Phase 1 | Early Rosettes | Oct4−, SSEA4− Pax 6+, Sox 1− nestin+ PSA-NCAM− | DMEM/F12 (1:1); N2 supplement; 2 ng/ml heparin, 10-20 ng/ml FGF2 | 5 days; media changed every 2 days; 25-$cm^2$ tissue culture flask; 36.5° C., 5% $CO_2$ | N/A |
| Phase 2 | Neural-like Tube Rosettes | Bf-1+, Otx2+ Nestin+, En1+, Pax2+ | 10-20 ng/ml FGF2 | 5-6 days; media changed every 2 days; 25-$cm^2$ tissue culture flask; 36.5° C., 5% $CO_2$ | N/A |
| Phase 2 | Neural epithelial cells ($2^{nd}$ Dispase Treatment) | N/A | 0.1-0.2 mg/ml dispase | 15-20 minutes; 36.5° C.; ambient atmosphere | N/A |
| Phase 2 | Expansion of neuroepithelial cells | Bf-1+, Otx2+ | DMEM/F12 (1:1); N2 supplement; 2 ng/ml heparin; 10-200 ng/ml FGF8 +50-250 ng/ml SHH | 5-6 days; media changed every 2 days; 25-$cm^2$ tissue culture flask; 36.5° C., 5% $CO_2$ | N/A |
| Phase 2 | $1^{st}$ dissociation | N/A | N/A | Accutase (Gibco) | N//A |
| Phase 2 | Forebrain DA neurons | TH+, AADC+, DbH−, PNMT−, Bf-1+, Otx2+, c-ret+, GABA+ | Neurobasal medium; N2; 0.1 mM non-essential amino acids; 0.5 mM glutamine; 1 µg/ml laminin; 1 µM cAMP; 200 µM ascorbic acid; 10 ng/ml BDGF; 0 ng/ml GDNF | 2-3 weeks; media changed every 2 days; culture Petri dishes; 36.5° C., 5% $CO_2$ | Secretion of DA, Action potentials. |

EXAMPLES

Example 1

Generation of Forebrain Dopaminergic Neurons

Results

Human ES cells differentiate to form neural tube-like structures in the presence of FGF2. Human ES cell lines, H1, H9 and a clonal line derived from H9, H9.2 (Amit, M., et al., supra, 2000) were propagated on a feeder layer of irradiated mouse embryonic fibroblasts (Thomson, J. A., et al., supra, 1998). To initiate differentiation, ES cell colonies were detached and grown in suspension as embryoid bodies (EBs) for four days. The EBs were then cultured in a tissue culture treated flask in a chemically defined medium (Zhang, S.-C., et al., *J. Neurosci. Res.* 59:421-429, 2000; Zhang, S.-C., et al., *Proc. Natl. Acad. Sci. USA* 96:4089-4094, 1999) containing FGF2. FGF2 was obtained from Peprotech, Inc., Rocky Hill, N.J. After five days of culture in FGF2, the plated EBs had generated an outgrowth of flattened cells. At the same time, an increasing number of small elongated cells was noted in the center of the differentiating EBs (FIG. 1A). By seven days in the defined medium, the central, small, elongated cells had generated rosette formations (FIG. 1B) resembling the early neural tube as shown by toluidine blue-stained sections (inset in FIG. 1B). Immunofluorescence analyses revealed that the expression of neural marker antigens nestin and Musashi-1 (Lendahl, U., et al., *Cell* 60:585-595, 1990; Kaneko, Y., et al., *Dev. Neurosci.* 22:139-153, 2000), was largely restricted to cells in the rosettes but not the flat cells in the periphery of the differentiating EBs (FIG. 1C-E). Undifferentiated ES cells were immunonegative for these markers. The formation of neural tube-like structures was noted in the majority of EBs in the presence of FGF2 (94% of the total 350 EBs from H9 and H9.2 lines, 3 separate experiments). In the absence of FGF2, no well organized rosettes were observed.

Neural tube-like rosettes can be isolated by differential enzymatic treatment and adhesion. With continued exposure to FGF2, the columnar rosette cells expanded and formed multiple layers. They frequently made up most of the EB and were sharply demarcated from the surrounding flat cells. Treatment with dispase led to the preferential detachment of the central neuroepithelial islands, leaving the surrounding cells largely adherent (FIG. 1F). Contaminating single cells were separated by short-term adhesion to cell culture dishes. Cell counts performed immediately after this isolation and enrichment procedure showed that cells associated with the isolated neuroepithelial clusters made up 72~84% of the cells in the differentiated EB cultures. Immunocytochemical analyses showed that 96±0.6% of the isolated rosette cells were positively stained for nestin based on 13,324 cells examined in four separate experiments. The vast majority of these cells were also positive for Musashi-1 and PSA-NCAM (FIG. 1G, H, I).

Human ES cell-derived neural precursors generate all three CNS cell types in vitro. The isolated neural precursors were expanded as free-floating cell aggregates in a suspension culture, similar to "neurosphere" cultures derived from human fetal brain tissues (Zhang, S.-C., et al., supra, 2000; Svendsen, C. N., et al., supra, 1996; Carpenter, M. K., et al., supra, 1999; Vescovi, A. L., et al., supra, 1999). BrdU incorporation studies revealed that stimulation of precursor cell proliferation was dependent on FGF2 and could not be elicited by either EGF or LIF alone. Furthermore, no additive or synergistic effects were observed when FGF2 was combined with EGF and/or LIF (FIG. 2A).

In vitro differentiation of the ES cell-derived neural precursors was induced by withdrawal of FGF2 and plating on ornithine and laminin substrate. Within a few days, individual cells and numerous growth cones grew out from the spheres, giving a star burst appearance. By seven to ten days after plating, processes emanating from the spheres had formed prominent fiber bundles. Frequently, small migrating cells were seen in close association with the fibers (FIG. 2B). Immunofluorescence analyses of the differentiated cultures revealed that the vast majority of cells in the outgrowth areas expressed neuronal markers MAP2ab and $\square_{III}$-tubulin (FIG. 2C). Expression of low molecular weight neurofilament (NF) and high molecular weight NF was observed by seven to ten and ten to fourteen days after plating, respectively (FIG. 2D). Antibodies to various neurotransmitters were used to further characterize the ES cell-derived neurons. While the majority of the neurons exhibited a glutamatergic phenotype (FIG. 2E), a smaller proportion was labeled with an antibody to GABA. Frequently, these neurons showed a polar morphology (FIG. 2F). A small number of neurons were found to express TH (FIG. 2G), the rate-limiting enzyme for dopamine synthesis. GFAP$^+$ astrocytes were rarely found within the first two weeks after growth factor withdrawal (FIG. 2C), but became more frequent after prolonged in vitro differentiation. By four weeks, they had formed an extensive layer underneath the differentiated neurons (FIG. 2D). While oligodendrocytes were not observed under standard culture conditions, a few O4-immunoreactive cells with typical oligodendrocyte morphology were observed when the cells were cultured in the presence of platelet-derived growth factor A (Zhang, S.-C., et al., supra, 2000) for longer than two weeks (FIG. 2H). Thus, ES cell-derived neural precursors generate all three major cell types of the CNS.

Human ES cell-derived neural precursors migrate, incorporate, and differentiate in vivo. To assess the differentiation of human ES cell-derived neural precursors in vivo, we grafted them into the lateral ventricles of newborn mice (Flax, J. D., et al., Nat. Biotech. 16:1033-1039, 1998). The transplanted cells formed clusters in various regions of the ventricular system and incorporated in large numbers into a variety of host brain regions. Of twenty-two brains analyzed between one and four weeks after transplantation, intraventricular clusters and incorporated cells were found in nineteen and eighteen recipient brains, respectively. Individual animals analyzed after longer time periods showed that grafted cells were detectable for at least eight-weeks post transplantation. Cells within the clusters showed strong immunoreactivity to antibodies against nestin, $\beta_{III}$-tubulin and MAP2ab. Only a few cells in the aggregates expressed GFAP. Alkaline phosphatase and cytokeratine, markers typically expressed in undifferentiated ES cells and non-neural epithelia, were not detected within the clusters. No teratoma formation was observed.

Figure 3:
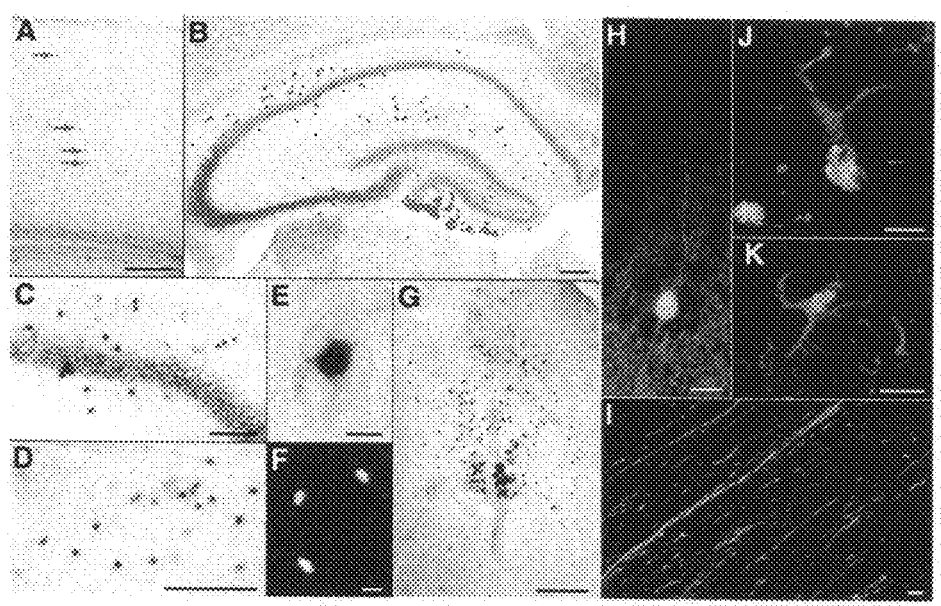

DNA in situ hybridization with a human-specific probe and immunohistochemical detection of a human nucleus-specific antigen revealed the presence of grafted cells in numerous brain regions. Gray matter areas exhibiting widespread donor cell incorporation included cortex (FIG. 3A), hippocampus (FIG. 3B,C), olfactory bulb, septum (FIG. 3D), thalamus, hypothalamus (FIG. 3E), striatum (FIG. 3F) and midbrain (FIG. 3G). Incorporation into white matter regions was most pronounced in the corpus callosum, internal capsule and hippocampal fiber tracts. Morphologically, the incorporated human cells were indistinguishable from the surrounding host cells and only detectable by the use of human-specific markers (FIG. 3). Double labeling with cell type-specific antibodies revealed that the incorporated cells had differentiated into both neurons and glia. Human ES cell-derived neurons could be clearly delineated with antibodies to $\beta_{IIIm}$-tubulin and MAP2 (FIG. 3H, J). Frequently, they displayed polar morphologies with long processes (FIG. 3H). In addition, neurons with multipolar and immature unipolar morphologies were found (FIG. 3J). The donor-derived neurons generated numerous axons projecting long distances into the host brain, which were detected in both gray and white matter. They were particularly abundant within fiber tracts such as the corpus callosum, the anterior commissure and the fimbria hippocampi where they could frequently be traced for several hundred micrometers within a single section (FIG. 3I)

In addition to neurons, a small number of ES cell-derived astrocytes was detected within the host brain tissue. They displayed stellate morphologies and exhibited strong expression of GFAP (FIG. 3K). In contrast, double labeling of incorporated human cells with antibodies to myelin proteins failed to detect mature oligodendrocytes. Some of the donor cells that had migrated into the host brain retained a nestin-positive phenotype even up to four weeks after transplantation. Many of these cells were found in perivascular locations.

Discussion

The present study indicates that engraftable neural precursors capable of generating mature neurons and glia can be generated with high yield from human ES cells. Exploiting growth factor-mediated proliferation/differentiation and differential adhesion of neural precursor cells, the in vitro differentiation procedure described herein provides a new platform for the study of neural development and the generation of donor cells for nervous system repair.

A key finding of this study is the observation that the differentiation of neural precursors from human ES cells appears to recapitulate early steps of nervous system development with the formation of neural tube-like structures in vitro. This phenomenon can now be exploited to study and experimentally manipulate the initial stages of human neural development under controlled conditions. The chemically defined culture system provides a unique opportunity to explore the effects of single factors on human neuroepithelial proliferation and specification in vitro. Similar to precursors derived from the developing human brain, human ES cell-derived precursors show a strong proliferative response to FGF2 (Flax, J. D., et al., supra, 1998). However, no additive or synergistic effects on proliferation can be elicited by EGF or LIF. This finding differs from data obtained with primary cells (Zhang, S.-C., et al., supra, 2000; Svendsen, C. N., et al., supra, 1996; Carpenter, M. K., et al., supra, 1999; Vescovi, A. L., et al., supra, 1999) and could suggest that proliferating ES cell-derived neural precursors represent a more immature stage than precursor cells derived from the fetal human brain. Studies on rodent cells indeed indicate that neural stem cells isolated from early neurogenesis depend on FGF2 for proliferation and the responsiveness to EGF is acquired only at later stages of neural precursor cell differentiation (Kalyani, A. D., et al., *Dev. Biol.* 186:202-223, 1997; Fricker, R. A., et al., *J. Neurosci.* 19:5990-6005, 1999).

The in vitro generation of neural tube-like structures and the possibility to isolate these structures based on their differential adhesion provides a simple yet efficient approach for generating human ES cell-derived neural precursors in high purity. Specifically, the strong cell-cell contacts within the neuroepithelial structures and their low adhesiveness to the tissue culture substrate permits the selective isolation of neural cells without significant contamination of undifferentiated ES cells or cells of other somatic lineages. The high efficiency of this procedure is reflected by the fact that more than 95% of the isolated cells exhibit a nestin-positive phenotype and no ES cells or non-neural epithelia are detectable in transplanted recipients. Since undifferentiated ES cells and precursors to other lineages may form tumors and foreign tissues, the generation of purified somatic cell populations is a key prerequisite for the development of ES cell-based neural transplant strategies.

Following transplantation into the neonatal mouse brain, the ES cell-derived neural precursors incorporated into a large variety of brain regions where they differentiated into neurons and glia. The failure to detect mature oligodendrocytes in vivo is likely due to the low oligodendroglial differentiation efficiency of human neural precursors as opposed to their rodent counterparts (Svendsen, C. N., et al., *Brain Pathol.* 9:499-513, 1999). Remarkably, donor-derived neurons were not restricted to sites exhibiting postnatal neurogenesis but were also found in many other regions of the brain. Similar data were obtained in studies involving transplantation of human CNS-derived precursors into the adult rodent brain (Tropepe, V., et al., *Dev. Biol.* 208:166-188, 1999). The incorporation of individual precursor cells into post-mitotic brain regions is particularly relevant with respect to cell replacement in the adult brain and spinal cord. Yet, more detailed studies will be required to determine whether and to what extent the incorporated cells acquire region-specific properties and become functionally active.

With the exception of intraventricular clusters composed of mature and immature neuroepithelial cells, no space-occupying lesions were detected within the host brains. Most notably, no teratoma formation was observed during a post-operative period up to eight weeks. While it is clear that more rigorous long-term safety studies particularly in non-human primates will be required before considering potential clinical applications, our data indicate that neural precursors isolated from differentiating human ES cells cultures represent a promising donor source for neural repair.

Experimental Protocols

Culture of ES cells. ES cells, H1 (passage 16 to 33), H9 (p34 to 55) and a clonal line derived from H9, H9.2 (p34 to 46) (Amit, M., et al., supra, 2000) were cultured on a feeder layer of irradiated mouse embryonic fibroblasts with a daily change of a medium that consisted of Dulbecco's modified Eagle's medium (DMEM)/F12, 20% serum replacement (Gibco), 0.1 mM β-mercaptoethanol, 2 µg/ml heparin, and 4 ng/ml of FGF2 (PeproTech Inc., Rochy Hill, N.J.) as previously described (Thomson, J. A., et al., supra, 1998). Karyotype analysis indicated that the lines at the given passages were diploid.

Differentiation cultures of ES cells. ES cell cultures were incubated with dispase (Gibco BRL, 0.1 mg/ml) at 37° C. for 30 minutes, which removed ES cell colonies intact. The ES cell colonies were pelleted, resuspended in ES cell medium without FGF2, and cultured for four days in a 25-cm$^2$ tissue culture flask (Nunc) with a daily medium change. ES cell colonies grew as floating EBs whereas any remaining feeder cells adhered to the flask. The feeder cells were removed by transferring the EBs into a new flask. EBs (~50/flask) were then plated in a 25-cm$^2$ tissue culture flask (Nunc) in DMEM/F12, supplemented with insulin (25 µg/ml), transferrin (100 µg/ml), progesterone (20 nM), putrescine (60 µM), sodium selenite (30 nM), and heparin (2 µg/ml) in the presence of FGF2 (20 ng/ml) (Zhang, S.-C., et al., supra, 2000; Zhang, S.-C., et al., supra, 1999).

Isolation and culture of neural precursor cells: To separate the clusters of rosette cells from the surrounding flat cells, the cultures were incubated with 0.1 mg/ml dispase at 37° C. for 15-20 minutes. The rosette clumps retracted whereas the surrounding flat cells remained adherent. At this point, the rosette clumps were dislodged by swaying the flask, which left the flat cells adherent. The clumps were pelleted, gently triturated with a 5-ml pipette and plated into a culture flask for 30 minutes to allow the contaminating individual cells to adhere. The floating rosette clumps were then transferred to a new flask coated with poly-(2-hydroxyethyl-methacrylate) to prohibit attachment and cultured in a medium used for human neural precursors (Zhang, S.-C., et al., supra, 2000) with the presence of FGF2 (20 ng/ml). To quantify the efficiency of neural differentiation and isolation, freshly separated cell clusters and the flat cells left behind were dissociated with trypsin (0.025% in 0.1% EDTA) and counted. The percentage of putative neural precursors (rosette cells) among the total cells differentiated from ES cells was obtained based on 3 independent experiments on H9 and H9.2 lines. For analyses of the differentiation potential of the ES cell-derived neural precursors, cells were cultured on ornithine/laminin substrate in a medium consisting of DMEM/F12, N2 supplement (Gibco), cAMP (100 ng/ml), and BDNF (10 ng/ml, Pepro-Tech) without the presence of FGF2. For oligodendrocyte differentiation, the ES cell-derived neural precursors were cultured in DMEM supplemented with N1 (Gibco) and platelet derived growth factor A (PDGFA) (2 ng/ml) as described (Zhang, S.-C., et al., supra, 2000). Morphological observation and immunostaining with markers for precursors and more matured neural cells were performed during the course of differentiation.

Histochemical and immunohistochemical staining. To better visualize the rosette formations, cultures with rosettes were rinsed with PBS and fixed in 4% paraformaldehyde and 0.25% glutaraldehyde for 1 hour. The fixed cells were then processed for embedding in plastic resin as described (Zhang, S.-C., et al., supra, 1999). The cultured cells were then sectioned in 1-µm thickness and stained with toluidine blue. For immunostaining, the coverslip cultures were immunostained with the following primary antibodies detected by appropriate fluorescent secondary antibodies detailed elsewhere (Zhang, S.-C., et al., supra, 2000; Zhang, S.-C., et al., supra, 1999): anti-nestin (polyclonal, gift of Dr. R. McKay of NINDS, 1:1,000); anti-polysialylated neuronal cell adhesion molecule (PSA-NCAM, mouse IgM, gift of Dr. G. Rougon of University of Marseille, France, 1:200); anti-Musashi-1 (rat IgG, gift of Dr. H. Okano, University of Tokyo, Japan, 1:500); anti-GFAP (polyclonal, Dako, 1:1,000); anti-human GFAP (Sternberg monoclonals, 1:10,000); O4 (mouse IgM, hybridoma supernatant, 1:50); anti-tyrosine hydroxylase (TH, Pel Freez, 1:500). The remaining antibodies were from Sigma: anti-$\beta_{III}$-tubulin (mouse IgG, 1:500); anti-neurofilament (NF) 68 (mouse IgG, 1:1,000); anti-NF 200 (polyclonal, 1:5, 000); anti-MAP2ab (mouse IgG, 1:250); anti-γ-aminobutyric acid (GABA, polyclonal, 1:10,000); anti-glutamate (mouse IgG, 1:10,000). For bromodeoxyuridine (BrdU) incorporation, 4 coverslip cultures in each group were incubated with 2 µM of BrdU for sixteen hours before the cultures were fixed in 4% paraformaldehyde, denatured with 1N HCl and processed for immunolabeling and cell counting (Zhang, S.-C., et al., supra, 2000; Zhang, S.-C., et al., supra, 1999).

Intracerebroventricular transplantation and in vivo analysis. A suspension of 100,000 viable cells/µL was prepared in L15 medium (Gibco) after dissociating aggregates of neural precursors with trypsin (0.025% in 0.1% EDTA at 37° C. for 5-10 minutes). Using illumination from below the head, 2~3 µL of cell suspension was slowly injected into each of the lateral ventricles of cryoanesthetized newborn mice (C3HeB/FeJ). The grafted animals were immunosuppressed by daily injection of cyclosporin A (10 mg/kg, i.p.). One, two, four, and eight weeks following transplantation, mice were perfused transcardially with Ringer's followed by 4% paraformaldehyde. Brains were dissected and post-fixed in the same fixative at 4° C. until use. Donor cells were identified in 50-µm coronal vibratome-sections by in situ hybridization using a digoxigenin-labeled probe to the human alu repeat element (Brustle, O., et al., Nat. Biotech. 16:1040-1044, 1998) or an antibody to a human-specific nuclear antigen (MAB1281, Chemicon, 1:50). Immunopositive cells were double labeled with antibodies to GFAP (1:100), nestin, $\beta_{III}$-tubulin (TUJ1, BabCo, 1:500), MAP2ab (Sigma, clones AP-20 and HM-2, 1:300), and phosphorylated medium molecular weight human neurofilament (clone HO-14, 1:50, a gift of J. Trojanowski). Primary antibodies were detected by appropriate fluorophore-conjugated secondary antibodies. Sections were analyzed on Zeiss Axioskop 2 and Leica laser scan microscopes.

Example 2

Generation of Midbrain Dopaminergic Neurons

A first step toward potential application of stem cell therapy in neurological conditions is the directed differentiation of neural cells with correct positional and transmitter phenotypes. Here we show a robust generation of functional dopaminergic (DA) neurons from human embryonic stem (ES) cells through a specific sequence of morphogen actions. Treatment of human ES-derived neuroectodermal cells at an early stage, before the expression of Sox1, with FGF8 is essential for specification of DA neurons with correct midbrain DA projection neuronal phenotypes. The in vitro generated DA neurons may be used for toxicological and pharmaceutical screening and for potential cell therapy in Parkinson's disease.

Parkinsons' disease (PD) results from progressive degeneration of DA neurons in the midbrain, especially the substantia nigra. Current therapy for PD relies primarily on symptom relief by systemic administration of DA precursors such as levadopa. Such therapy is effective for the first few years but almost invariably loses its efficacy and produces serious side effects. Administration of growth factors such as glial cell line-derived neurotrophic factor (GDNF) has been shown to be effective in a small clinical trial (Gill, S. S., et al., Nat. Med. 9:589-595, 2003). This therapy would depend on a sufficient number of surviving DA neurons, and its long-term therapeutic potential remains to be investigated. Because of the focal nature of neuronal degeneration, cell transplantation has been proposed as an alternative therapy (Bjorklund, A. and Lindvall, O., Nat. Neurosci. 3:537-544, 2000). In some successful cases, transplanted fetal midbrain cells survive for over a decade and contribute to the relief of symptoms (Kowdower, J. H., et al., N. Engl. J. Med. 332:1118-1124, 1995; Piccini, P., et al., Nat. Neurosci. 2:1137-1140, 1999), although the recent controlled clinical trials cast doubt on the efficacy of fetal tissue transplant therapy for PD (Freed, C. R., et al., N. Engl. J. Med. 344:710-719, 2001; Olanow, C. W., et al., Ann. Neurol. 54:403-414, 2003). These phenomena are indicative of the complexity of PD. A reliable, renewable source of functional human midbrain DA neurons is urgently needed for a systematic study of the genesis of the DA system, pathogenic process affecting the survival and function of DA neurons, and development of the sustainable therapeutics for PD.

It has been shown that DA neurons can be efficiently generated from mouse ES cells, which are derived from the inner cell mass of pre-implantation embryos at the blastocyst stage (Evans, M. J. and Kaufman, M. H., Nature 292:154-156, 1981; Martin, G. R., Proc. Natl. Acad. Sci. USA 78:7634-7638, 1981). Mouse ES cells are first induced to neuroectodermal cells by FGF2 (Lee, S. H., et al., Nat. Biotechnol. 18:675-679, 2000) or by stromal cell-derived inducing activity (Kawasaki, H., et al., Neuron 28:31-40, 2000; Barberi, T., et al., Nat. Biotechnol. 21:1200-1207, 2003). The neuroectodermal cells are subsequently exposed to FGF8 followed by SHH for DA neuron induction. In this study, we have established a robust system to induce human ES cells (Thomson, J. A., et al., Science 282:1145-1147, 1998) to differentiate into neuroectodermal cells (Zhang, S. C., et al., Nat. Biotechnol. 19:1129-1133, 2001) that, in response to FGF8 and SHH, generated a large proportion of DA neurons with midbrain projection characteristics. We have found that, in order to generate DA neurons with midbrain projection neuronal phenotypes, human ES cells require exposure to FGF8 before precursor cells become Sox1$^+$ expressing neuroectodermal cells.

Results

Human ES-derived neuroectodermal cells display a forebrain character. ES cell colonies, detached from a feeder layer, were cultured in suspension as aggregates for four days in ES cell growth medium, and then grown in an adhesive culture dish in a chemically defined neural medium containing FGF2 (20 ng/ml) (Zhang, S. C., et al., supra, 2001). Cells in the colony center developed a columnar morphology and lined up in a rosette formation around day nine (FIG. 4A). These columnar cells were positive of Pax6, but negative for the pan-neural transcription factor Sox1 (not shown), indicative of early neuroectodermal cells. Over another five to six days (day 14-15), the columnar cells expanded and organized into neural tube-like rosettes (FIG. 4B), and expressed Sox1 (FIG. 4C), a transcription factor expressed by definitive neuroectodermal cells during neural tube closure (Pevny, L. H., et al., Development 125:1967-1978, 1998). They were positive for brain factor (Bf1), a transcription factor expressed by forebrain cells (Tao, W. and Lai, E., Neuron 8:057-966, 1992), but negative for engrailed 1 (En-1) (FIG. 4D), a transcription factor expressed by midbrain cells (Davidson, D., et al., Development 104:305-316, 1988; Wurst, W., et al., Development 120:2065-2075, 1994), suggesting a forebrain identity of the in vitro generated neuroectodermal cells.

Induction of midbrain phenotype requires early action of FGF8. For differentiation to DA neurons, neuroectodermal cells in the neural tube-like rosettes were enriched through differential enzymatic and adhesion treatment (Zhang, S. C., et al., supra, 2001), expanded for four days as aggregates in suspension with FGF2, and were then plated onto a laminin substrate and treated with SHH (50-200 ng/ml) and FGF8 (20-100 ng/ml) for six days. Immunocytochemical analyses revealed that the vast majority of the neuroectodermal cells remained positive for Bf1 but not for En-1 (not shown).

The failure of FGF8 to induce Sox1$^+$ neuroectodermal cells to express En-1 suggests that the Sox1-expressing neuroectodermal cells may be refractory to patterning signals. Since the Sox1-expressing cells are generated two weeks after differentiation of human ES cells (equivalent to a six-day-old embryo (Thomson, J. A., et al., supra, 1998)) and formed neural tube-like structures, they may correspond to the neuroectodermal cells at neural tube closure during which neuroectodermal cells express Sox1 and are regionally specified (Lumsden, A. and Krumlauf, R., Science 274:1109-1115, 1996). This led us to hypothesize that FGF8 may promote midbrain specification before neuroectodermal cells express Sox1. We thus applied FGF8 (100 ng/ml) at the time when the cells in the colony center became columnar at day nine. After six days, cells in the colony center developed neural tube-like formations, as seen in the presence of FGF2. These neuroectodermal cells were similarly enriched, expanded in FGF8 for four days, and then treated with SHH for six days on the laminin substrate. Under this culture condition, En-1 expression was observed in the nestin-expressing neuroectodermal cells (FIG. 4E), although there were still cells that expressed Bf1 (FIG. 4F). Thus, neuroectodermal cells were efficiently regionalized before they become Sox1$^+$.

Regionalized neuroectodermal cells differentiate into DA neurons. The neuroectodermal cells were dissociated and differentiated in a neural differentiation medium. They did not express stage specific embryonic antigen 4 (SSEA4), a glycoprotein highly expressed by undifferentiated human ES cells. The disaggregated neuroectodermal cells, initially distributed evenly, re-formed rosettes three to five days after plating. They then extended processes and exhibited polar morphology. At three weeks after differentiation, about one third of the total differentiated cell population (31.8±3.1% TH$^+$ cells of 17,965 counted from four experiments) were positive for tyrosine hydroxylase (TH) (FIG. 5A). A similar percentage of TH$^+$ cells was obtained from both H9 and H1 human ES cell lines. Most TH-expressing cells were 10-20 μm in diameter. They exhibited multipolar morphology, with differentiable axons and dendrites (FIG. 5A). All the TH$^+$ cells were stained positively with a neuronal marker $\beta_{III}$-tubulin$^+$ neurons, about 50% were TH$^+$ (FIG. 5B, 6,383 TH$^+$ cells of 12,859 $\beta_{III}$-tubulin$^+$ neurons from four experiments).

In the biosynthesis of monoamines, TH hydroxylates tyrosine to L-DOPA, which is subsequently decarboxylated to become DA by AADC. Another two enzymes, DβH and phenylethanolamine N-methyltransferase (PNMT), transform DA to norepinephrine and catalyze norepinephrine to epinephrine, respectively. Immunostaining showed that all TH$^+$ cells were AADC (FIG. 5C-E) although some AADC$^+$ cells were negative for TH (FIG. 5E). However, TH$^+$ cells were negative for DβH (FIG. 5F) and PNMT (not shown), although DβH strongly stained noradrenergic neurons in the adult rat and embryonic monkey brainstem (inset in FIG. 5F). These data suggest that the TH-expressing neurons possess both enzymes that are necessary for dopamine synthesis, and that these neurons are DA neurons rather than noradrenergic or adrenergic neurons.

ES cell-generated DA neurons display midbrain phenotypes. RT-PCR analyses indicated that Nurr1, Limx1b, En-1 and Ptx3, which are involved in midbrain DA neuron development (Zetterstrom, R. H., et al., Science 276:248-250, 1997; Smidt, M. P., et al., Proc. Natl. Acad. Sci. USA 94:13305-13310, 1997; Saucedo-Cardenas, O., et al., Proc. Natl. Acad. Sci. USA 95:4013-4018, 1998; Wallen, A., et al., Exp. Cell Res. 253:737-746, 1999; Smidt, M. P., et al., Nat. Neurosci. 3:337-341, 2000; Simon, H. H., et al., J. Neurosci. 21:3126-3134, 2001; Van den Munckhof, P., et al., Development 130:2535-2542, 2003; Nunes, I., et al., Proc. Natl. Acad. Sci. USA 100:4245-4250, 2003), were not expressed at a high level until neuroectrodermal cells were differentiated into DA neurons (FIG. 6A). Immunostaining revealed that most TH$^+$ cells with multiple processes co-expressed the midbrain marker En-1 in the nuclei (FIG. 6B). Thus, DA neurons generated using the above approach possess a midbrain positional identity.

DA neurons in the olfactory bulb often co-express γ-aminobutyric acid (GABA) (Kosaka, T., et al., Exp. Brain Res. 66:191-210, 1987; Gall, C. M., et al., J. Comp. Neurol. 266: 307-318, 1987). Double immunostaining of TH and GABA indicated that most of the DA neurons were negative for GABA although GABA$^+$ neurons were found in the culture (FIG. 6C). Among all TH$^+$ cells, 8% (8.7±3.9%, 6,520 TH$^+$ cells counted from four experiments) of TH$^+$ cell co-expressed GABA. Most of these double positive cells were small bipolar cells (inset in FIG. 6C). Some midbrain DA neurons, especially those in the ventral tegmental area, co-express cholecystokinin octapeptide (CCK8) or calbindin along with TH (McRitchie, D. A., et al., J. Comp. Neurol. 364:121-150, 1996; Hokfelt, T., et al., Neurosci. 5:2093-2124, 1980). Immunohistochemical analyses indicated that the TH$^+$ neurons were observed (FIG. 6D). These calbindin neurons were mostly small cells. No CCK8 positive cells were detected in the cultures.

ES cell-generated DA neurons are biologically functional. Immunostaining showed that all TH$^+$ neurons expressed c-Ret, a component of the receptor for GDNF (FIG. 7A-C). The majority of the TH$^+$ cells, especially those with branched neurites, expressed vesicular monoamine transporter 2 (VMAT2, FIG. 7D-F), which is responsible for packaging dopamine into subcellular compartments in monoamine neurons (Nirenberg, M. J., et al., J. Neurosci. 16:4135-4145, 1996). In addition, TH$^+$ neurons expressed synaptophysin, a membrane glycoprotein essential to synapse formation (Calakos, N. and Scheller, R. H., J. Biol. Chem. 269:24534-24537, 1994) (FIG. 7A-I).

Dopamine release is a functional hallmark of DA neurons. High performance liquid chromatography (HPLC) analyses revealed the presence of dopamine in the medium of DA differentiation cultures, with 230.8±44.0 pg/ml in the cultures treated with ascorbic acid (AA), FGF8 and SHH and 46.3±9.2 pg/ml in the control cultures without the treatment of AA, FGF8 and SHH (FIG. 8A). When cultured cells were washed and incubated in HBSS for fourteen minutes, the dopamine level was similar between the two cultures (FIG. 8A). However, depolarization of the cultured neurons by 56 mM KCl in HBSS significantly increased the amount of DA (35.8±9.2 and 111.0±15.0 pg/ml in the cultures without and with AA, FGF8 and SHH treatment, respectively; FIG. 8A). These observations suggest that the in vitro generated DA neurons can secrete DA and the release of DA is activity-dependent.

Electrophysiological recordings were used to determine whether ES-generated DA neurons were functionally active. In cells maintained in culture for thirty to thirty-eight days (n=14), the resting membrane potential ($V_{rest}$) ranged from −32 to −72 mV (−54±2.9 mV), cell capacitance ($C_m$) ranged from 11 to 45 pF (21±2.7 pF), and input resistance ($R_{in}$) ranged from 480 to 3500 MΩ (1506±282 MΩ). Depolarizing current steps (0.2 nA×200-500 ms) usually elicited single action potentials, but in several cases decrementing trains of action potentials were observed (FIGS. 8bi and ii). Action potential (AP) threshold ranged from −26 to −5.2 mV (−17.4±2.1 mV), and peaked at −9.6 to 30 mV. AP's up to 50.2 mV were observed (32±2.8 mV). AP duration ranged from 3 to 20.6 ms (7.2±1.3 ms). Spontaneous firing was observed in two cells (FIG. 8C).

In voltage clamp mode, both inward and outward currents were observed in all cells (not shown), but their relative magnitudes varied considerably. Inward currents were activated rapidly (<1 ms), and peaked within 1-3 ms. Activation threshold was −30±1 mV, maximal peak current amplitude was obtained at a mean voltage of −13±1.9 mV, and currents were completely blocked by tetrodotoxin (TTX, n=3). These properties are consistent with the presence of voltage-gated sodium channels that underlie action potential generation. In three cells we observed spontaneous transient currents that had the characteristics of synaptic currents, including a rapid rise and slower decay phase. One of these recordings was made with a K-gluconate based pipette solution, and holding this cell at −40 mV allowed us to observe both outward (inhibitory) and inward (excitatory) currents (FIGS. 8di and dii). Although all fourteen cells were injected with biocytin, only five cells were recovered after the completion of the immunostaining procedures. However, all of the five biocytin-filled cells were labeled TH (FIG. 8E-G).

Discussion

We have demonstrated here that functional DA neurons with midbrain neuronal projection characteristics can be efficiently generated from human ES cells through three simple non-genetic steps: induction of neuroectodermal cells with FGF2, specification of ventral midbrain identity by FGF8 and SHH during neuroectodermal formation, and differentiation of the regionally specified progenitors to DA neurons. Unlike the findings obtained from mouse ES cell studies in which DA neurons with midbrain characteristics can be generated from expanded neuroectodermal cells (Lee, S. H., et al., supra, 2000), we have found that specification or regionalization with FGF8 before precursor cells become Sox1$^+$ neuroectodermal cells is essential for a robust generation of human DA neurons with correct midbrain and functional phenotypes.

From the standpoint of stem cell biology, it seems very logical to direct mouse ES cells to neuroectodermal cells, expand them, regionalize or specify them with FGF8 and SHH, and subsequently differentiate them into DA neurons, a stepwise protocol developed by McKay and colleagues (Lee, S. H., et al., supra, 2000). We hypothesized that the same principle should apply to human primates. Indeed, we are able to generate a large number of DA neurons by differentiating human ES cells into neuroectodermal cells that express Sox1 and organize into neural tube-like rosettes in the presence of FGF2 (Zhang, S. C., et al., supra, 2001), treating the neuroectodermal cells with FGF8 and SHH to induce a ventral midbrain fate and finally differentiating the cells into neurons. However, most of the DA neurons generated in this way lack some of the key characteristics of midbrain projection DA neurons, e.g., large size with complex morphology and expression of midbrain transcription factors at the protein level. The Sox1 positive neuroectodermal cells, even after treatment with FGF8 and SHH, are still negative for En-1 but positive for Bf1, suggesting the Sox1-expressing neuroectodermal cells are refractory for specification to a midbrain fate. The process of neuroectodermal differentiation from human ES cells in our culture system parallels what is seen during in vivo development (Zhang, S. C., supra, 2003). In vivo, the neural tube forms at the end of third week of human gestation and Sox1 is expressed by the neuroectoderm during neural tube closure based on mouse embryological study (Pevny, L. H., et al., Development 125:1967-1978, 1998). In culture, the neuroectodermal cells form neural tube-like rosettes and express Sox1 after two weeks of differentiation from human ES cells that are equivalent to a six-day-old human embryo (Thomson, J. A., et al., supra, 1998). The projection neurons, including midbrain DA neurons, are differentiated from neuroectodermal cells in the neural tube at the early stage and these neuroectodermal cells are already regionally specified during the process of neural tube closure (Lumsden, A. and Krumlauf, R., supra, 1996). This may explain why the human ES cell-generated Sox1-expressing neuroectodermal cells that possess forebrain phenotypes are not responsive to morphogens for generating DA neurons with midbrain phenotypes. Our hypothesis that FGF8 may instruct the early precursors to adopt a midbrain identify is confirmed by the generation of DA neurons that have characteristics of projection neurons such as large cell bodies with complex processes and expression of midbrain makers En1, after the Sox1$^-$ columnar cells in the early rosettes are treated with FGF8.

It is presently not clear why FGF2-induced mouse ES cell-, but not human ES cell-derived neuroectodermal cells, can be efficiently regionalized after expansion. There is recent evidence that the dorsal or ventral identity of neural progenitors isolated from mouse spinal cord may be deregulated upon culture, especially in the presence of FGF2 (Gabay, L., et al., Neuron 40:485-499, 2003), which may partly account for the capability of expanded mouse ES-derived neuroectodermal cells to be respecified. Our studies on the differentiation of other projection neurons such as spinal motor neurons are consistent with the present observation that generation of large projection neurons requires early action of morphogens.

DA neurons are present in several areas of the brain, including midbrain, hypothalamus, retina, and olfactory bulbs. The human ES cell-generated DA neurons in this study resemble midbrain projection DA neurons. Most of the DA neurons do not co-express GABA, whereas co-expression of GABA and TH is a major feature of olfactory DA interneurons (Kosaka, T., et al., supra, 18987; Gall, C. M., et al., supra, 1987). In the midbrain, there are at least two major groups of DA neurons, those in the substantia nigra (A9) and in the ventral tegmental area (A10), each having different targets (Bjorklund, A. and Lindvall, O., Handbook of Chemical Neuroanatomy, Vol. 2: Classical Transmitters in the CNS (Bjorklund, A., Hokfelt, T., eds), Amsterdam, Elsevier Science Publishers, pp. 55-111, 1984). Most DA neurons in the ventral tegmental area express calbindin or CCK, whereas few in the substantial nigra do (McRitchie, D. A., et al., J. Comp. Neurol. 364:121-150, 1996; Hokfelt, T., et al., Neurosci. 5:2093-2124, 1980; Haber, S, N., et al., J. Comp. Neurol. 362:400-410, 1995). Our observation that the human ES cell-generated DA neurons do not co-express TH with CCK8 or calbindin suggests that these DA neurons resemble more closely the substantia nigra DNA neurons.

The robust capability of human ES cells to generate large projection neurons with an appropriate regional identity such as midbrain DA neurons opens up an unprecedented opportunity to dissect the early phase of neural development using the human ES cell system. Our data demonstrates a requirement for morphogens, such as FGF8, to act on early neuroectodermal cells, which are unspecified, for the generation of early born midbrain projection DA neurons. This may explain why stem cells or progenitors isolated and expanded from embryonic and adult mammalian brains that are already specified are refractory to generate projection neurons (Svendsen, C. N., et al., *Exp. Neurol.* 148:135-146, 1997; Daadi, M. M. and Weiss, S., *J. Neurosci.* 19:4484-4497, 1999; Storch, A., et al., *Exp. Neurol.* 170:317-325, 2001). The in vitro generated human DA neurons also offer a system for toxicological and pharmaceutical screening for chemicals and drugs that may affect human DA neurons. Studies are underway to determine whether these human DA neurons generated in an culture Petri dish are functional in PD animal models.

Methods

ES cell cultures. Human ES cell lines, H9 (p21-56) and H1 (p35-40), were propagated weekly on irradiated mouse embryonic fibroblasts (MEF) with a daily change of an ES cell growth medium that consisted of Dulbecco's modified Eagle's medium (DMEM)/F12 (Gibco), 20% serum replacer (Gibco), 1 mM glutamine (Sigma), 0.1 mM non-essential amino acids (Gibco), 2 µg/ml of heparin (Sigma), 0.1 mM β-mercaptoethanol (sigma), and 4 ng/ml of FGF2 (R & D Systems), as described by Thomson (Thomson, J. A., et al., supra, 1998). Differentiated colonies were physically removed using a curved Pasteur pipette and the undifferentiated state of ES cells was confirmed by typical morphology and immunostaining with Oct4 and SSEA4.

Differentiation and enrichment of neuroectodermal cells. Human ES cell colonies were detached from MEF layer by the treatment of the culture with 0.2 mg/ml of dispase (Roche Diagnositics) and grown as floating cell aggregates (embryoid body) for four days with a daily change of ES cell medium. They were then grown in an adherent substrate in a neural medium consisting of DMEM/F12 (2:1), supplemented with N2 (Gibco), 0.1 mM non-essential amino acids, 2 µg/ml heparin with a medium change every other day. The ES cell aggregates attached and formed individual colonies at around day six. Neuroectodermal cells, exhibited by columnar cells organizing into neural tube-like rosettes, were developed at around day fourteen (Zhang, S. C., et al., supra, 2001). The neural rosettes were isolated through differential enzymatic response (Zhang, S. C., et al., supra, 2001). Growth factors were added during the course of differentiation to influence regionalization (see results).

DA neuron differentiation. The enriched neuroectodermal cells were dissociated by 0.025% trypsin and 0.27 mM EDTA in PBS at 37° C. for 10-15 minutes and plated onto 12-mm coverslips (pre-coated with 100 µg/ml polyornithine and 10 µg/ml laminin) at a density of 40,000-50,000 cells/coverslip. The neuronal differentiation medium consisted of neurobasal medium (Gibco) supplemented with N2, 0.1 mM non-essential amino acids, 0.5 mM glutamine, 1 µg/ml laminin, 1 µM cAMP, 200 µM AA (Sigma), 10 ng/ml BDNF (R & D Systems) and 10 ng/ml GDNF (R & D Systems). The cells were cultured for three to four weeks with medium change every other day.

Immunocytochemistry and cell quantification. Coverslip cultures were fixed in 4% paraformaldehyde in PBS for 10-20 minutes or methanol (−20° C.) for 5 minutes and processed for immunostaining (Zhang, S. C., et al., supra, 2001). The following primary antibodies were used: mouse anti-SSEA4 (1:40), mouse anti-En-1 (1:50) and mouse anti-Pax6 (1:5000, all from Developmental studies hybridoma bank); rabbit anti-Sox 1 (1:500), rabbit anti-human nestin (1:200), rabbit anti-AADC (1:1000), sheep anti DβH, (1:400), mouse anti-synaptophysin (1:500) and rabbit anti-CCK8 (1:2000, all from Chemicon); mouse anti-TH (1:1000), mouse anti-βIII tubulin (1:500), rabbit anti-GABA (1:5000) and mouse anti-calbindin (1:400, all from Sigma); rabbit anti-TH (1:500) and rabbit anti-VMAT2 (1:500, all from Pel-Freez); Goat anti-c-Ret (1:400) and mouse anti-Oct4 (1:1000, both from Santa Cruz); rabbit anti-Bf1 (1:5000; gift from Lorenz Studer). Antibody-antigen reaction was revealed by appropriate fluorescence-conjugated secondary antibody. Cell nuclei were stained with Hoechst 33342. Staining was visualized with a Nikon fluorescence microscope. Brain sections from adult rats and E38 embryonic monkeys were used as positive controls for many of the antibodies against neuronal types and neurotransmitters. Negative controls were also set by omitting the primary or secondary antibodies in the immunostaining procedures. Cell counting was achieved blindly by using a reticule on eyepiece and a 40× objective. The cells in ten visual fields were randomly selected and counted from each coverslip.

RT-PCR. Total RNA was extracted from cultured cells using RNA Stat-60 (Tel-Test, Friendswood, Tex.), followed by the treatment with DNase I (DNA-free, Ambion). Synthesis of cDNA was carried out with the Superscript First-Strand Synthesis System for RT-PCR (Invitrogen) according to the manufacturer's directions. PCR amplification was performed using a standard procedure with Taq Polymerase (Promega). The number of cycles varied from 25 to 35 cycles depending on the particular mRNA abundance with denaturation at 94° C. for 15 seconds, annealing temperatures at 55° C. or 60° C. for 30 seconds according to the primers, and elongation at 72° C. for 45 seconds. Negative control was achieved by omitting transcriptase during reverse transcription or cDNA sample during PCR. The primers and product lengths were as follows: GAPDH (5'-ACCACAGTCCATGCCATCAC-3' (SEQ ID NO: 1), 5'-TCCACCACCCTGTTGCTGTA-3' (SEQ ID NO: 2), 450 bp); Nurr1 (5'-CGATGCCTTGTGTTCAG-GCGCAG-3' (SEQ ID NO: 3), 5'-AGCCTTTGCAGCCCT-CACAGGTG-3' (SEQ ID NO: 4), 858 bp); Ptx3 (5'-GTGGGTGGAGAGGAGAACAA-3' (SEQ ID NO: 5), 5'-TTCCTCCCTCAGGAAACAATG-3' (SEQ ID NO: 6), 175 bp); Lmx1b (5'-GGGATCGGAAACTGTTACTGC-3' (SEQ ID NO: 7), 5'-GTAGTCACCCTTGCACAGCA-3' (SEQ ID NO: 8), 218 bp); En-1 (5'-CCCTGGTTTCTCTGG-GACTT-3' (SEQ ID NO: 9), 5'-GCAGTCTGTGGGGTCG-TATT-3' (SEQ ID NO: 10), 162 bp).

DA measurement. After twenty-one days of DA neuronal differentiation, media conditioned for forty-eight hours were collected. Activity-dependent dopamine release from the cultured cells was measured by first conditioning cultured cells in Hank's balanced salt solution (HBSS) for 15 minutes and then replacing it with HBSS containing 56 mM KCl for 14 minutes at 37° C. Dopamine in the culture media or in HBSS was stabilized by adding 20 µl stabilization buffer (900 mg EGTA and 700 mg gluthathione in 10 ml of 0.1 M NaOH) and samples were stored in −80° C. A HPLC kit (Chromsystems) was used to extract monoamines. The levels of monoamines were determined by HPLC (Model 508 autosampler and model 118 pump, Beckman) coupled to electrochemical detector (Coulochem II, ESA Inc.) by using MD-TM mobile phase (ESA Inc.). The cultures in each group were triplicated and data were collected from three separate experiments.

Electrophysiological recording. Electrophysiological properties of the DA neurons differentiated from human ES cells were investigated using whole-cell patch-clamp recording techniques (Hammill, O. P., et al., *Pflugers Arch.* 391:85-100, 1981). Pipettes were filled with intracellular solutions containing (mM) KCl 140 or K-gluconate 140, Na$^+$-HEPES 10, BAPTA 10, Mg$^{2+}$-ATP 4, (pH 7.2, 290 mOsm, 2.3-5.0 MΩ). Biocytin (0.5%, Sigma) was added to the recording solution and subsequent labeling with streptavidin-Alex Flur 488 (1:1000, Molecular Probes) and an antibody against TH was used to identify DA neurons. The bath solution contained (in mM) NaCl-127, KH$_2$PO$_4$ 1.2, KCl 1.9, NaHCO$_3$ 26, CaCl$_2$ 2.2, MgSO$_4$ 1.4, glucose 10, 95% O$_2$/5% CO$_2$ (pH 7.3, 300 mOsm). For some experiments, TTX (1 µm) was applied in the bath solution to block voltage-gated sodium currents.

Current-clamp and voltage-clamp recordings were performed using a MultiClamp 700A amplifier (Axon Instruments). Signals were filtered at 4 kHz, sampled at 10 kHz using a Digidata 1322A analog-digital converter (Axon Instruments), and acquired and stored on a computer hard disk using commercially available software (pClamp9, Axon Instruments). Access resistance was typically 8-18 MΩ and was compensated by 50-80% using amplifier circuitry. Voltages were corrected for liquid junction potential of +13 mV (Neher, E., *Methods Enzymol.* 207:123-131, 1992). V$_{rest}$ and action potentials were examined in current-clamp mode. Spontaneous excitatory (inward) and inhibitory (outward) synaptic currents were characterized in voltage-clamp mode using K-gluconate based pipette solution and V$_{hold}$=−40 mV. Synaptic events were detected using a template detection algorithm (Mini Analysis Program 4.6.28, Synaptosoft) and deactivation phase was fitted to a biexponential function using the Levenberg-Marquardt algorithm. Data are presented as mean ±SE.

Example 3

Generation of Motor Neurons

Generation of motor neurons in vertebrate animals involves at least three steps: neuralization of ectodermal cells, caudalization of the neuroectodermal cells, and ventralization of the caudalized neural progenitors (Jessell, T. M., *Nat. Rev. Genet.* 1:20-29, 2000). We first established a culture system for efficient neuroectodermal differentiation from hES cells (Thomson, J. A., et al., *Science* 282:1145-1147, 1998) (H1 and H9 lines) using an adherent colony culture in the presence of FGF2 (Zhang, S. C., et al., *Nat. Biotechnol.* 19:1129-1133, 2001), based on the principle that vertebrate neuroectoderm develops in response to FGF and/or anti-BMP (bone morphogenetic protein) signals (Wilson, S. I. and Edlund, T., *Nat. Neurosci.* 4:Suppl.:1161-1168, 2001). The first sign of neural differentiation was the appearance of columnar cells forming rosettes in the center of colonies 8-10 days after ES cells were removed from feeder cells for differentiation. The columnar cells in the rosettes, but not the flat cells in the outgrowth area, expressed a neuroectoderm marker Pax6 but not the pan-neuroectodermal transcription factor Sox1 (FIG. 9A), which is expressed by neuroepithelial cells during neural tube formation (Pevny, L. H., et al., *Development* 125:1967-1978, 1998). With further culturing in the same medium for another four to five days, the columnar cells organized into neural tube-like rosettes with lumens (FIG. 9B) and expressed both Pax6 and Sox1 (FIG. 9C, D). Thus, differentiation of neuroectodermal cells from hES cells involves at least two distinctive stages, the Pax6$^+$/Sox1$^-$ columnar cells in the early rosettes eight to ten days after neural induction, and the Pax6$^+$/Sox1$^+$ cells forming neural tube-like late rosettes fourteen days after induction.

Immunocytochemical analyses revealed that the rosette cells, which expressed Pax6 (FIG. 9E), Sox1, and nestin, were positive for Otx2 (FIG. 9F, H), a homeodomain protein expressed by fore- and mid-brain cells; but negative for HoxC8 (FIG. 9H), a homeodomain protein produced by cells in the spinal cord. They were also negative for En1, which is expressed by midbrain cells (FIG. 9G). These results suggest that the neuroectodermal cells possess a forebrain phenotype, similar to that initially acquired by neuroectodermal cells during early in vivo development (Stern, D. C., *Nat. Rev. Neurosci.* 2:92-98, 2001).

To differentiate motor neurons from neuroectodermal cells, Sox1$^+$ neuroectodermal cells in the neural tube-like rosettes were isolated through enzymatic treatment (Zhang, S. C., et al., *Nat. Biotechnol.* 19:1129-1133, 2001) and differentiated on the laminin substrate in the presence of retinoic acid (RA, 0.001-1 µM), a caudalizing reagent (Blumberg, B., et al., *Development* 124:373-379, 1997), and SHH (50-500 ng/ml), a ventralizing morphogen (Jessell, T. M., *Nat. Rev. Genet.* 1:20-29, 2000; Briscoe, J. and Ericson, J., *Curr. Opin. Neurobiol.* 11:43-49, 2001). By fourteen days after plating, a large number of cells in the outgrowth area formed a network through their processes (FIG. 10A). Immunostaining analyses indicated that the differentiated cells were positive for neuronal markers β$_{III}$-tubulin and MAP2. A large proportion (>50%) of them were also positive for Isl 1 (FIG. 10A) and Lim3 (not shown), transcription factors that are associated with motor neuron development (Jessell, T. M., supra; Briscoe, J. and Ericson, J., supra, 2001; Shirasaki, R. and Pfaff, S. L., *Annu. Rev. Neurosci.* 25:251-281, 2002). However, very few cells in cultures between one to three weeks expressed HB9 (FIG. 10A), a motor neuron-specific transcription factor (Arber, S., et al. *Neuron* 23:659-674, 1999). These suggest that the Sox1$^+$ neuroectodermal cells may be refractory for motor neuron induction.

The Sox1-expressing cells may correspond to neuroectodermal cells in the neural tube given the formation of neural tube-like rosettes and expression of Sox1 at a time equivalent to a three-week-old human embryo. The neuroectodermal cells in the neural tube are regionally specified (Lumsden, A. and Krumlauf, R., *Science* 274:1109-1115, 1996). This consideration led us to hypothesize that RA may promote caudalization and/or motor neuron specification before neuroectodermal cells express Sox1. We thus treated the neuroectodermal cells with RA (0.001-1 µM) at an earlier stage, i.e., when columnar cells began to organize into rosettes and expressed Pax6. Cultures treated in this way for 6 days developed into neural tube-like rosettes and expressed Sox1, indistinguishable from FGF2 treated cultures. After the rosette clusters were isolated and adhered to the laminin substrate, numerous neurites extended from the cluster as early as twenty-four to forty-eight hours after plating. By fourteen days after plating, the neurite outgrowth area covered almost the entire (11-mm diameter) coverslip although there were limited numbers of neuronal cell bodies in the outgrowth area (FIG. 10A). The majority of cells were positive for Isl 1/2, among which about 50% were also HB9$^+$ (FIG. 10B), suggesting that these double positive cells are motor neurons. The Isl 1/2$^+$ and HB9$^+$ cells were likely interneurons.

HB9-expressing cells first appeared at day six and reached a high proportion around day ten to twelve after the neural rosettes were plated for differentiation. They were largely localized to the cluster, with about 21% of the total cells in the cluster and few cells in the outgrowth area (FIG. 10A, D). The highest proportion of HB9$^+$ cells was induced in the presence of 0.1-1.0 µM of RA. RA at the dose over 1.0 µM resulted in degeneration of some cells in our chemically defined adherent cultures. In the absence of RA, or SHH, or both, there were very few HB9$^+$ cells (FIG. 10D). All the HB9-expressing cells were stained with β$_{III}$-tubulin (FIG. 10C). Thus treatment with RA on early neuroectodermal cells is required for efficient induction of motor neurons.

To understand why RA induces early but not late neuroectodermal cells to differentiate into motor neurons, we first examined the effect of RA on caudalization of the neuroectodermal cells. Treatment of early rosette cells (Pax6$^+$/Sox1$^-$) with RA (0.001-1.0 μM) or FGF2 (20 ng/ml) for seven days resulted in the decreased expression of Otx2 and increased expression of Hox genes such as Hox B1, B6, C5, and C8 in a dose-dependent manner (FIG. 11A). Genes expressed by more caudal cells were induced by higher doses of RA. Treatment of late rosette cells (Pax6$^+$/Sox1$^+$) with RA for one week did not alter the Hox gene expression pattern induced by FGF2 (not shown). The RA-treated early rosette cells, isolated and cultured in the neuronal differentiation medium, expressed HoxC8 protein first at day six and mostly at day ten to twelve after differentiation, as revealed by immunocytochemistry (FIG. 11D). Cells at this stage lacked Otx2 expression (FIG. 1 IC). All the HoxC8$^+$ cells were ($\beta_{III}$-tubulin$^+$ neurons (FIG. 11E). In contrast, late rosette cells treated with RA for one week and then differentiated for two weeks, yielded few HoxC8$^+$ cells, although Otx2-expressing cells were decreased (not shown). Thus treatment of early but not late neuroectodermal cells with RA results in efficient caudalization with expression of HoxC proteins, which are associated with spinal motor neurons (Liu, J. P., et al., *Neuron* 32:997-1012, 2001).

We then compared the effect of SHH on early and late neuroectodermal cells for ventralization. The hES cell-derived neuroectodermal cells, whether they were Pax6$^+$ or Sox1$^+$, did not express Olig2 (FIG. 11F), a homeodomain protein expressed in ventral neural progenitor cells that are destined to become motor neurons and oligodendrocytes in the spinal cord (Lu, Q. R., et al., *Cell* 109:75-86, 2002; Zhou, Q., et al., *Neuron* 31:791-807, 2001). When the Pax6$^+$/Sox1$^-$ neuroectodermal cells were cultured in the presence of RA for one week, then isolated and further differentiated for another two weeks in the absence of SHH, very few cells expressed Olig2 (not shown). However, in the presence of SHH (50-500 ng/ml), many cells expressed Olig2 in the nuclei (FIG. 11G). In contrast, Pax6$^+$/Sox1$^+$ neuroectodermal cells, differentiated for two weeks under the same condition, generated few Olig2-expressing cells (FIG. 11H). Thus, neuroectodermal cells, treated with RA at an early but not the late stage, can be efficiently induced to a ventral neural progenitor fate in response to SHH.

To further discern why early RA treatment is required for motor neuron specification even though FGF2 also induces a caudal fate (FIG. 11A), we examined the expression of Class I (Irx3, Pax6) and Class II (Olig2, Nkx2.2, Nkx6.1) molecules that are important in refining progenitor domains in the spinal cord (Jessell, T. M., supra, 2000; Briscoe, J., and Ericson, J., supra, 2001). RA induced a much more robust expression of SHH and Class II genes particularly Olig2 and Nkx6.1 in early than in late neuroectodermal cells (FIG. 11B). Thus, early neuroectodermal cells are more responsive to RA in upregulating the expression of SHH and Class II factors, which are essential for motor neuron specification.

Cells that expressed choline acetyltransferase (ChAT) appeared three weeks after the caudalized neuroectodermal cells were plated for motor neuron differentiation and these cells increased steadily for up to seven weeks, the longest culture period analyzed in this study (FIG. 12A). The ChAT-expressing cells were largely localized to the cluster (FIG. 12A), corresponding to the localization of the HB9$^+$ cells. These cells were mainly multipolar cells and had large somas of 15-20 μm in diameter, with some being as big as 30 μm (FIG. 12A, B). Co-expression of HB9 in the nuclei and ChAT in the soma and processes was observed after three weeks of culture (FIG. 12C). Most of the neurons were also positively stained for vesicular acetylcholine transporter (VAChT, FIG. 12D), which is essential for storage and release of acetylcholine. Many ChAT$^+$ cells, especially after five weeks in culture, were positively labeled for synapsin on cell bodies and processes (FIG. 12E).

We assessed functional maturation using electrophysiological techniques (n=28 cells). The mean resting potential was −36.9±2.6 mV and input resistance was 920±57 MΩ. Single action potentials (AP's, FIG. 13Ai) or decrementing trains (FIG. 13Aii) were elicited by depolarizing current steps (0.15-0.2 nA×1 s) in eleven of thirteen neurons tested. Spontaneous AP's triggered by spontaneous depolarizing synaptic inputs were also observed (FIG. 13B). Although not all cells survived recording and subsequent immunohistochemical analysis, double immunostaining with biocytin and ChAT demonstrated that many of the cells from which we recorded were motor neurons (FIG. 13E-G).

Voltage clamp analysis revealed time- and voltage-dependent inward and outward currents consistent with sodium and delayed rectifier potassium currents. Inward currents and action potentials were blocked by 1.0 μM tetrodotoxin (TTX, n=3), confirming the presence of voltage-activated sodium channels. Outward currents were not further characterized. We also observed spontaneous synaptic currents (FIG. 13C, n=21 of 23 cells tested). These were reduced in frequency but not eliminated by 1.0 μM TTX, demonstrating the existence of functionally intact synaptic neurotransmission. With a CsGluconate-based pipette solution, outward (inhibitory) currents decayed slowly (13.6 ms, n=10 events) and were blocked by a combination of strychnine and bicuculline, whereas the remaining inward (excitatory) currents decayed rapidly (2.1 ms, n=17 events) and were blocked by a combination of D-AP5 and CNQX (FIG. 13C, E-G), demonstrating that inhibitory (GABA/glycine) and excitatory (glutamate) neurotransmission occur as in the intact spinal cord (Gao, B. X., et al., *J. Neurophysiol.* 79:2277-2287, 1998).

Our present study demonstrates that functional motor neurons can be efficiently generated from human ES cells through neuroectodermal differentiation by FGF2, specification and/or caudalization by RA during the late phase of neuralization, and subsequent differentiation to post-mitotic motor neurons in the presence of the ventralizing morphogen SHH. Thus, fundamental principles of neural development learned from animals may be applied to human primates and recapitulated in vitro. In contrast to a recent demonstration of motor neuron differentiation from mouse ES cells (Wichterle, H., et al., *Cell* 110:385-397, 2002), we have dissected out the process of neuroectodermal differentiation and discovered that specification of early-born projection neurons such as spinal motor neurons requires treatment with morphogens before precursors become Sox1− expressing neuroectoderm cells.

Mouse ES cells have been first directed to neuroectodermal cells which are then treated with morphogens such as FGF8 and SHH for differentiation into dopaminergic neurons (Barberi, T., et al., *Nat. Biotechnol.* 21:1200-1207, 2003; Lee, S. H., et al., *Nat. Biotechnol.* 18:675-679, 2000) or RA and SHH for motor neuron differentiation (Wichterle, H., et al., supra, 2002). These observations seem to fit the notion that neurons are specified from epithelium in the neural tube. Our present observations indicate that the hES-derived, Sox1-expressing neuroectodermal cells which also possess a forebrain phenotype are refractory to generate spinal motor neurons. The Sox1− expressing cells generated from hES cells in our culture system resemble those in the neural tube, as they form neural tube-like structures and express Sox1 after two weeks of differentiation from hES cells which are equivalent to a six-day-old human embryo (Zhang, S. C., *J. Hematother.*

*Stem Cell Res.* 12:625-634, 2003). In vivo, the neural tube forms at the end of third week of human gestation (Wood, H. B. and Episkopou, V., *Mech. Dev.* 86:197-201, 1999) and Sox1 is expressed by the neuroectoderm during the formation of the neural tube in animals (Pevny, L. H., et al., *Development* 125:1967-1978, 1998; Wood, H. B. and Episkopou, V., supra, 1999). Our finding suggests that the specification of a class of neurons, at least large projection neurons such as motor neurons, begins before stem cells become Sox1-expressing neuroectodermal cells and may thus explain why brain-derived neuroepithelial cells fail to generate projection neurons of a different regional identity.

The functional motor neurons from the renewable source of hES cells offer generic human motor neurons for screening pharmaceuticals designed for treating motor neuron-related disorders such as ALS. These cells also provide a useful source for experimental cell replacement for motor neurons, which may someday lead to applications in patients with motor neuron diseases or spinal cord injury.

Methods

Culture of ES cells and neural differentiation. Human ES cells (lines H1 and H9, passages 19 to 42) were cultured and passaged weekly on a feeder layer of irradiated embryonic mouse fibroblasts as described (Thomson, J. A., et al., supra, 1998). The undifferentiated state of ES cells were confirmed by typical morphology and expression of Oct4 and SSEA4. For neuroectodermal differentiation, hES cells were aggregated for four days and then cultured on an adhesive plastic surface for ten days in F12/DMEM supplemented with N2, heparin (2 ng/ml), and FGF2 (20 ng/ml) or RA (Zhang, S. C., et al., supra, 2001).

For motor neuron induction, the morphogen-treated neuroectodermal cells were plated onto ornithine/laminin-coated coverslips in a neuronal differentiation medium, which consisted of Neurobasal medium (Gibco), N2 supplement, and cAMP (Sigma, IgM) in the presence of RA (0.1 mM) and SHH (10-500 ng/ml, R&D) for one week. After that, BDNF, GDNF, and insulin-like growth factor-1 (IGF1) (10 ng/ml, PeproTech Inc.) were added to the medium and the concentration of SHH was reduced to 50 ng/ml.

Immunocytochemistry and microscopy (Zhang, S. C., et al. supra, 2001). Primary antibodies used in this study included polyclonal antibodies against neuronal class III β-tubulin (Covance Research Products, Richmond, Calif., 1:2000), nestin (Chemicon, Temecula, Calif., 1:750), Sox1 (Chemicon, 1:1000), synapsin I (Calbiochem, Darmstadt, German, 1:500), ChAT (Chemicon, 1:50), and VAChT (Chemicon, 1:1000), Isl1/2 (S. Pfaff), Otx2 (F. Vaccarino), and Olig2 (M. Nakafuku). Antibodies against MNR2 or HB9 (81.5C10), Islet1 (40.2D6), Lim3 (67.4E12), Pax6, and Nkx2.2, were purchased from Developmental Studies Hybridoma Bank (DSHB, Iowa City, Iowa), and anti-HoxC8 from Covance Research Products (1:200). For identification of electrophysiologically recorded cells, biocytin (Molecular Probes) filled cells were labeled with streptavidin-FITC (sigma, 1:200) and stained for ChAT. Images were collected using a Spot digital camera mounted onto a Nikon fluorescent microscope 600 (FRYER INC, Huntley, Ill.) or a confocal microscope (Nikon, Tokyo, Japan). The specificity of antibodies against motor neuron transcription factors and homeodomain proteins, which were originally developed against non-primate tissues, were verified in embryonic (E34 or E36) rhesus monkey spinal cord and brain tissues (provided by the Wisconsin Primate Research Center).

Quantification. The population of HB9-expressing cells among total differentiated cells (Hoechst labeled) was counted by a person who was blind to experimental groups either manually using the Metamorph software (Universal Imaging Corporation, Downingtown, Pa.) or by stereological measurement. An area to be measured was outlined by a tracer, with the number of counting frames preset so that the scope sampled the measuring sites randomly using an automated stage movement operated by Stereo Investigator software (MicroBrightField Inc, Williston, Vt.). For counting areas with overlapping cells, the microscope was preset to move up and down to focus on the positive cells in different layers and the total cell number in the cluster was estimated by the software. Three to four coverslips in each group were counted and data were expressed as Mean ±SD.

RT-PCR assays. RT-PCR amplifications were performed from hES cell-derived neuroectodermal cells at different stages and motor neuron differentiation cultures. The following primers were used: HoxC8,5'-TTTATGGGGCTCAG-CAAGAGG-3' (SEQ ID NO: 11), 5'-TCCACTTCATCCT-TCGGTTCTG-3' (SEQ ID NO: 12), 318 bp; HoxC5, 5'-TCGGGGTGCTTCCTTGTAGC-3' (SEQ ID NO: 13), 5'-TTCGTGGCAGGGACTATGGG-3' (SEQ ID NO: 14), 290 bp; HoxB6, 5'-AACTCCACCTTCCCCGTCAC-3' (SEQ ID NO: 15), 5'-CTTCTGTCTCGCCGAACACG-3' (SEQ ID NO: 16), 340 bp; Otx2, 5'-CAACAGCAGAATG-GAGGTCA-3' (SEQ ID NO: 17), 5'-CTGGGTGGAAA-GAGAAGCTG-3' (SEQ ID NO: 18), 429 bp; HoxBl, 5'-TCAGAAGGAGACGGAGGCTA-3' (SEQ ID NO: 19), 5'-GTGGGGGTGTTAGGTTCTGA-3' (SEQ ID NO: 20), 218 bp; GAPDH, 5'-ACCACAGTCCATGCCATCAC-3' (SEQ ID NO: 1), 5'-TCCACCACCCTGTTGCTGTA-3' (SEQ ID NO: 2), 450 bp; Olig2, 5'-AAGGAGGCAGTG-GCTTCAAGTC-3' (SEQ ID NO: 21), 5'-CGCTCAC-CAGTCGCTTCATC-3' (SEQ ID NO: 22), 315 bp; Nkx2.2, 5'-TGCCTCTCCTTCTGAACCTTGG-3' (SEQ ID NO: 23), 5'-GCGAAATCTGCCACCAGTTG-3' (SEQ ID NO: 24), 337 bp. lrx3,5'-AAGAACGCCACCAGGGAGAG-3' (SEQ ID NO: 25), 5'-TTGGAGTCCGAAATGGGTCC-3' (SEQ ID NO: 26), 473 bp; Pax6, 5'-GGCAACCTACGCAAGATGGC-3' (SEQ ID NO: 27), 5'-TGAGGGCTGTGTCTGTTCGG-3' (SEQ ID NO: 28), 459 bp; SHH, 5'-CCAATTACAAC-CCCGACATC-3' (SEQ ID NO: 29), 5'-CCGAGTTCTCT-GCTTTCACC-3' (SEQ ID NO: 30), 339 bp; Nkx6.1, 5'-ACACGAGACCCACTTTTTCCG-3' (SEQ ID NO: 31), 5'-TGCTGGACTTGTGCTTCTTCAAC-3' (SEQ ID NO: 32), 335 bp.

Electrophysiology recording. Electrophysiological properties of hES cell-derived motor neurons were investigated in cultures differentiated for five to six weeks using whole-cell patch-clamp recording techniques (Gao, B. X., et al., *J. Neurophysiol.* 79:2277-2287, 1998). Tetrodotoxin (TTX, 1 µM, Sigma), bicuculline (20 µM, Sigma), strychnine (5 µM, Sigma), D-2-amino-5-phosphonovaleric acid (AP-5, 40 µM, Sigma) or 6-cyano-7-nitroquinoxaline-2,3-dione (CNQX, 20 µM, RBI, Natick, Mass.) were applied in the bath solution to confirm the identity of voltage-activated or synaptic currents. For some experiments, 1% biocytin was added to the recording solution. Current- and voltage-clamp recordings were performed using a MultiClamp 700A amplifier (Axon Instruments, Union City, Calif.). Signals were filtered at 4 kHz, sampled at 10 kHz using a Digidata 1322A analog-digital converter (Axon Instruments), and acquired and stored on a computer hard disk using commercially available software (pClamp9, Axon Instruments). Access resistance was typically 8-15 MΩ and was compensated by 50-80% using amplifier circuitry. Spontaneous synaptic currents were detected using a template detection algorithm (Mini Analysis Program 5.6.28, Synaptosoft, Decatur, Ga.) and fitted to a monoexponential function using the Levenberg-Marquardt algorithm. Results are presented as mean ±SEM.

We claim:

1. A method of generating a population of human spinal motor neurons comprising:
   (a) culturing human Sox1$^-$, Pax6$^+$ cells characterized by an early rosette morphology for 4-6 days in the presence of retinoic acid (RA), wherein a population of Hox$^+$ cells are created;
   (b) culturing the cells resulting from step (a) in the presence of RA and sonic hedgehog (SHH); and
   (c) culturing the cells resulting from step (b) in neuronal differentiation medium and in the presence of SHH, wherein the resulting cells express HB9, HoxB1, HoxB6, HoxC5, HoxC8, choline acetyltransferase (ChAT) and vesicular acetylcholine transporter (VAChT) and produce acetylcholine.

2. The method of claim 1 wherein the cells are exposed to SHH between 6-7 days in step (b).

3. A population of human spinal motor neurons generated by the method of claim 1, wherein the spinal motor neurons express HB9, HoxB1, HoxB6, HoxC5, HoxC8, ChAT and VAChT and produce acetylcholine.

4. The method of claim 1 wherein the cells are exposed to SHH between 6-10 days in step (b).

5. The method of claim 1 wherein the cells are exposed to neuronal differentiation medium between 7-21 days in step (c).

* * * * *

UNITED STATES PATENT AND TRADEMARK OFFICE
CERTIFICATE OF CORRECTION

| | | |
|---|---|---|
| PATENT NO. | : 7,972,850 B2 | Page 1 of 1 |
| APPLICATION NO. | : 11/594455 | |
| DATED | : July 5, 2011 | |
| INVENTOR(S) | : Su-Chun Zhang et al. | |

It is certified that error appears in the above-identified patent and that said Letters Patent is hereby corrected as shown below:

Column 1, lines 22-23 "This invention was made with no United States government support." should be -- This invention was made with government support under grant number NS045926 awarded by the National Institutes of Health. The government has certain rights in this invention. --

Signed and Sealed this
Twenty-seventh Day of September, 2011

David J. Kappos
*Director of the United States Patent and Trademark Office*

UNITED STATES PATENT AND TRADEMARK OFFICE
CERTIFICATE OF CORRECTION

PATENT NO.        : 7,972,850 B2
APPLICATION NO.   : 11/594455
DATED             : July 5, 2011
INVENTOR(S)       : Su-Chun Zhang et al.

It is certified that error appears in the above-identified patent and that said Letters Patent is hereby corrected as shown below:

Column 3, line 21 "cells are $\beta_{II}$-tubulin $^+$neurons" should be -- cells are $\beta_{III}$-tubulin$^+$ neurons --Column 10, line 7 "CHAT" should be -- ChAT --

Column 19, line 34 " $\square_{III}$ " should be -- $\beta_{III}$ --

Column 22, line 16 "2 $\square$g/ml" should be -- 2 $\mu$g/ml --

Column 22, line 57 " 1-$\square$m" should be -- 1-$\mu$m --

Signed and Sealed this
Eighth Day of November, 2011

David J. Kappos
*Director of the United States Patent and Trademark Office*